United States Patent
Zhang et al.

(10) Patent No.: US 12,364,734 B2
(45) Date of Patent: Jul. 22, 2025

(54) METHODS OF TREATING ALZHEIMERS DISEASE

(71) Applicant: NUtech Ventures, Lincoln, NE (US)

(72) Inventors: Luwen Zhang, Lincoln, NE (US); Chi Zhang, Omaha, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 18/417,206

(22) Filed: Jan. 19, 2024

(65) Prior Publication Data

US 2024/0197819 A1 Jun. 20, 2024

Related U.S. Application Data

(62) Division of application No. 17/369,681, filed on Jul. 7, 2021, now Pat. No. 11,911,437.

(60) Provisional application No. 63/049,039, filed on Jul. 7, 2020.

(51) Int. Cl.
*A61K 38/16* (2006.01)
*A61P 25/28* (2006.01)

(52) U.S. Cl.
CPC ............ *A61K 38/162* (2013.01); *A61P 25/28* (2018.01)

(58) Field of Classification Search
CPC ....... A61K 38/162; A61K 38/16; A61P 25/28; Y02A 50/30
See application file for complete search history.

(56) References Cited

U.S. PATENT DOCUMENTS

2017/0312354 A1 11/2017 Paessler et al.
2021/0054055 A1 2/2021 Diehl et al.

FOREIGN PATENT DOCUMENTS

WO WO 2023/164441 8/2023

OTHER PUBLICATIONS

Alz.org [online], "Brain Tour: Slide 9," available on or before May 17, 2018, via Internet Archive: Wayback Machine URL <http://web.archive.org/web/20180517021518/https://www.alz.org/braintour/healthy_vs_alzheimers.asp>, retrieved on Jun. 13, 2022, URL< http://www.alz.org/braintour/healthy_vs_alzheimers.asp>, 2 pages.
Baig et al., "Use of Peptides for the Management of Alzheimer's Disease: Diagnosis and Inhibition," Front Aging Neurosci, Feb. 2018, 10(21): 6 pages.
Beys-da-Silva et al., "Zika Virus Infection of Human Mesenchymal Stem Cells Promotes Differential Expression of Proteins Linked to Several Neurological Diseases," Molecular Neurobiology, Oct. 2018, 56:4708-4717, 11 pages.
Brookmeyer et al., "Forecasting the global burden of Alzheimer's disease," Alzheimers Dement., Jul. 2007, 3(3):186-191.
CDC.gov [online], "Alzheimer's Disease and Related Dementias," Oct. 2020, retrieved on Jun. 13, 2022, retrieved from URL<cdc.gov/aging/aginginfo/alzheimers.htm#How>, 2 pages.
Gabriele et al., "Knockdown of Amyloid Precursor Protein: Biological Consequences and Clinical Opportunities," Frontiers in Neuroscience, Mar. 2022, 16:835645, 14 pages.
Hurd et al., "Monetary Costs of Dementia in the United States," NEJM, Apr. 2013, 368(14):1326-34.
Lingel et al., "Amyloid precursor protein is a restriction factor that protects against Zika virus infection in mammalian brains," J. Biol. Chem. in Press, Oct. 2020, 27 pages.
Lingel et al., "Amyloid precursor protein is a restriction factor that protects against Zika virus infection in mammalian brains," J. Biol. Chem., 2020, 295(50):17114-17127.
Matthews et al., "Racial and ethnic estimates of Alzheimer's disease and related dementias in the United States (2015-2060) in adults aged ≥65 years," Alzheimer's & Dementia, Jan. 2019, 15(1):17-24, 8 pages.
Mattson, "Pathways towards and away from Alzheimer's disease," Nature, Aug. 2004, 430(7000):631-639.
MayoClinic.org [online], "Alzheimer's disease," Feb. 2022, retrieved on Jun. 13, 2022, retrieved from URL<mayoclinic.org/diseasesconditions/alzheimers-disease/symptoms-causes/syc-20350447>, 8 pages.
MerckManuals.com [online], "Alzheimer Disease," Nov. 2018, retrieved on Apr. 21, 2023, retrieved from URL<https://www.merckmanuals.com/professional/neurologic-disorders/delirium-and-dementia/alzheimer-disease>, 10 pages.
Xu et al., "Deaths: Final Data for 2007," National Vital Statistics Reports, May 2010, 58(19): 135 pages.
Zhang, "Seminar Program: Amyloid Precursor Protein is a restriction factor for Zika virus in the brains," Seminar Program, Presented at University of Nebraska—Lincoln School of Biological Sciences Center for Virology, Lincoln, NE, May 3, 2019, 2 pages.

*Primary Examiner* — Julie Ha
(74) *Attorney, Agent, or Firm* — Fish & Richardson P.C.

(57) ABSTRACT

Methods and materials for treating a mammal having Alzheimer's disease (AD) are described. For example, one or more Zika virus (ZIKV) polypeptides can be administered to a mammal having, or at risk of developing, AD to treat the mammal.

3 Claims, 25 Drawing Sheets
(11 of 25 Drawing Sheet(s) Filed in Color)
Specification includes a Sequence Listing.

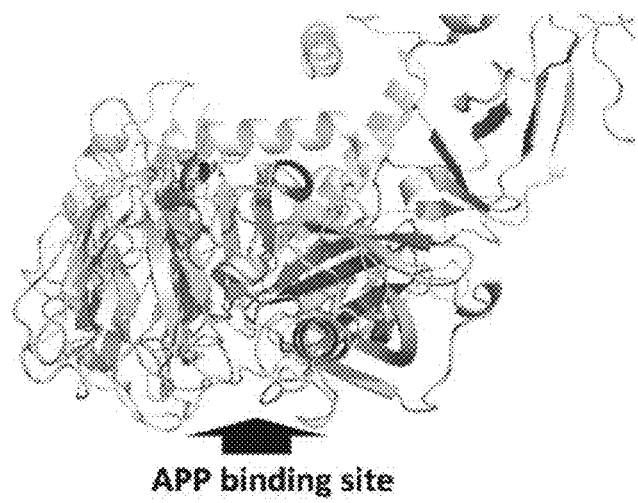
FIG. 1A
FIG. 1B
FIG. 1C
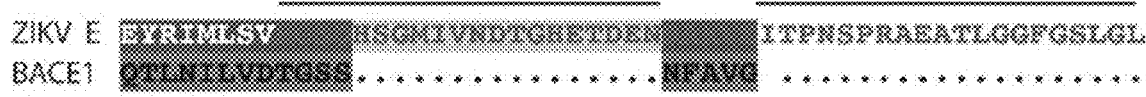

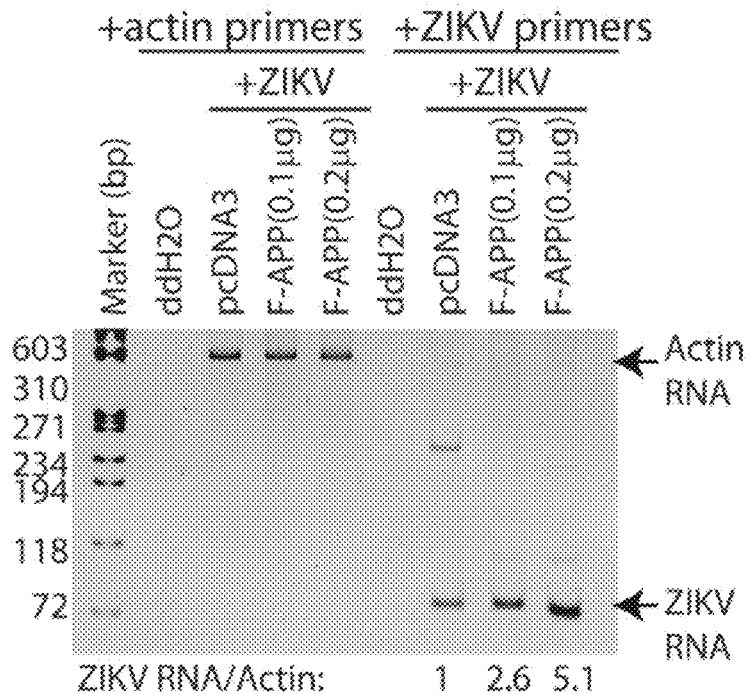
FIG. 1D
FIG. 1E
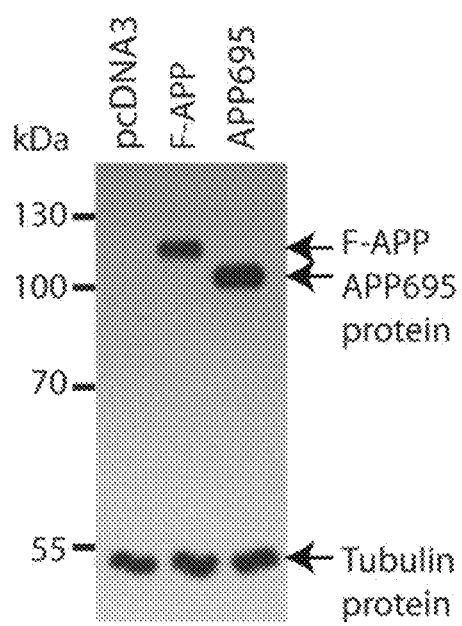
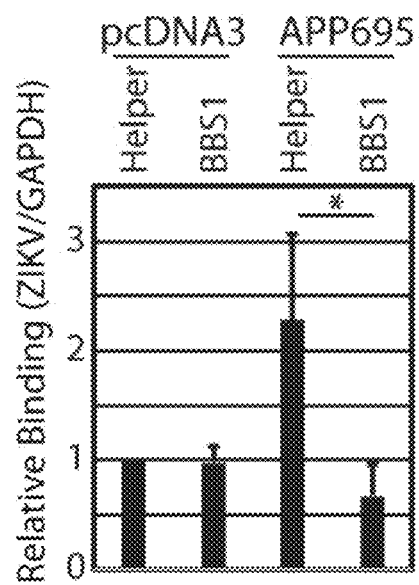
FIG. 1F
FIG. 1G

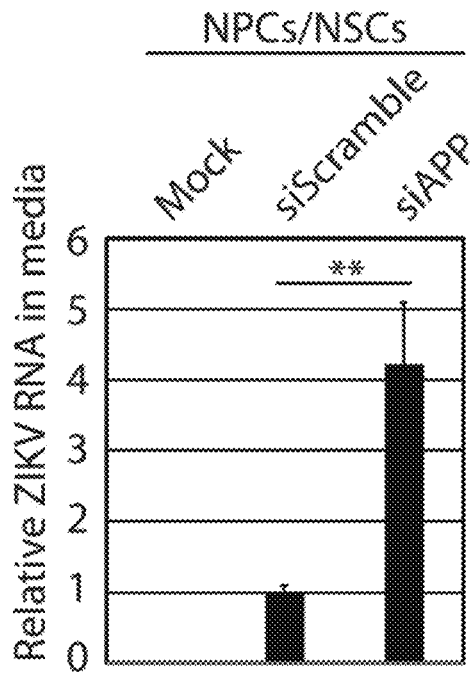
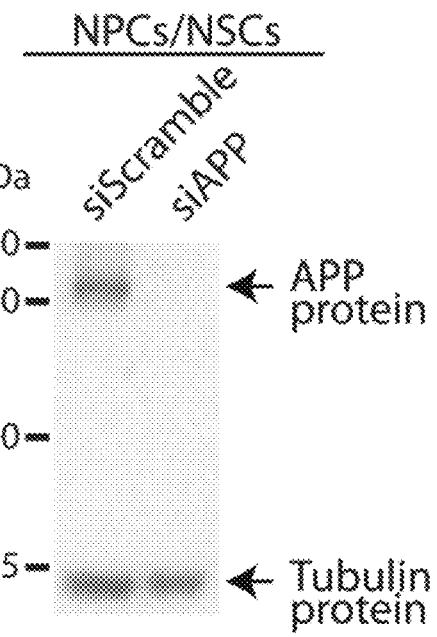
FIG. 3A
FIG. 3B
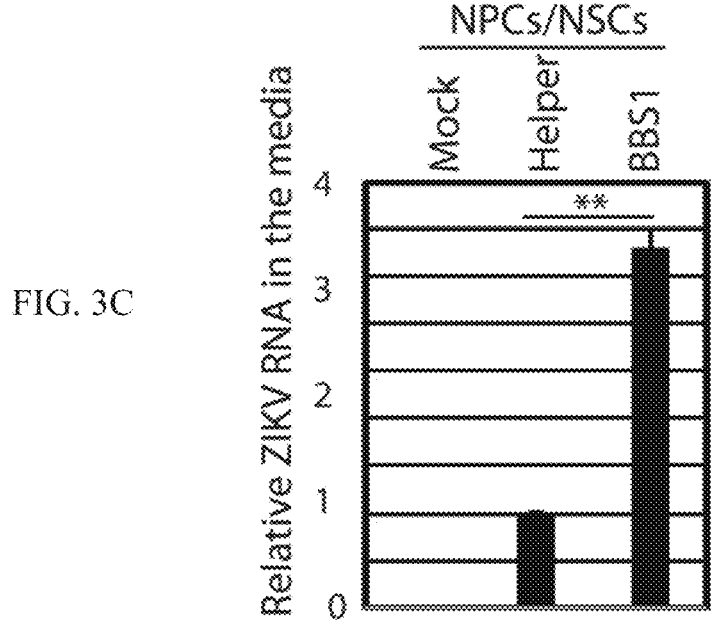
FIG. 3C

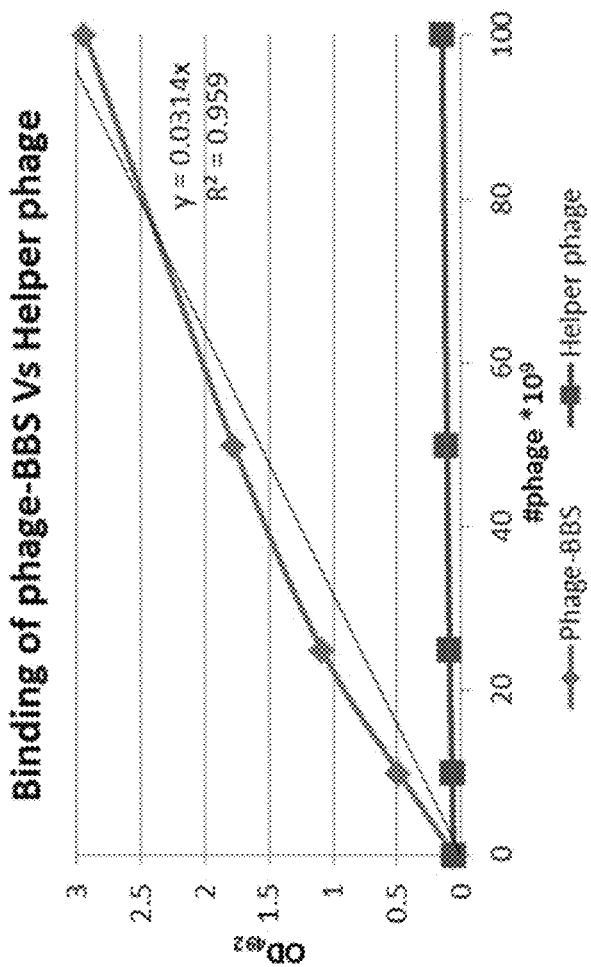
FIG. 5C
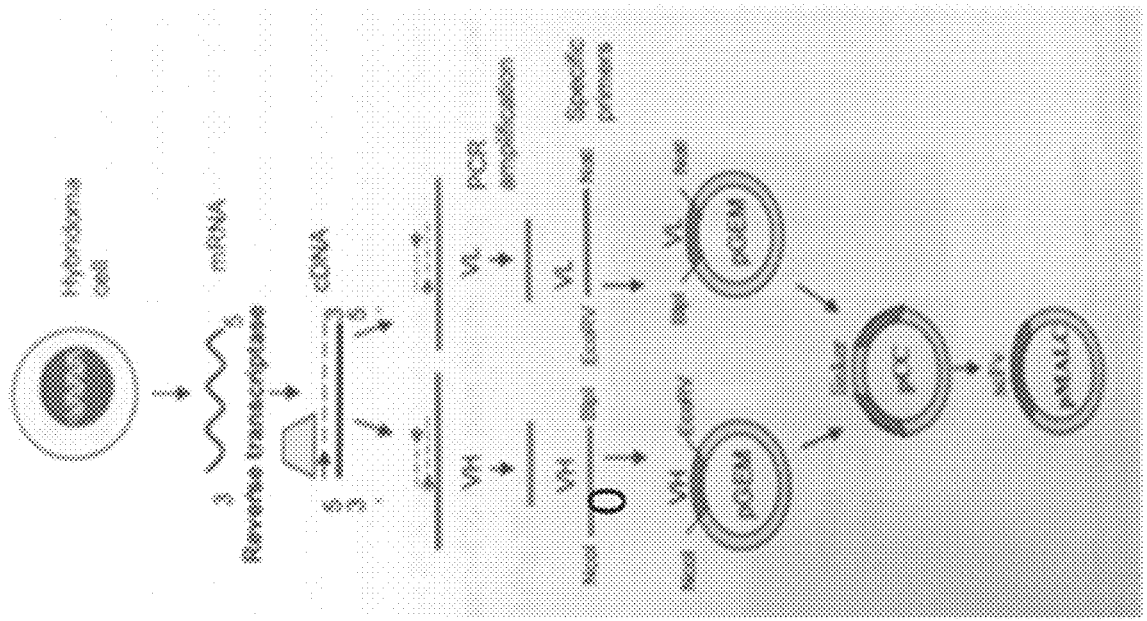

SEQUENCE LISTING

```
Sequence total quantity: 20
SEQ ID NO: 1            moltype = AA  length = 45
FEATURE                 Location/Qualifiers
source                  1..45
                        mol_type = protein
                        organism = Zika virus
SEQUENCE: 1
HGSQHSGMIV NDTGHETDEN RAKVEITPNS PRAEATLGGF GSLGL                   45

SEQ ID NO: 2            moltype = AA  length = 45
FEATURE                 Location/Qualifiers
source                  1..45
                        mol_type = protein
                        organism = Zika virus
SEQUENCE: 2
HGSQHSGMIV NDTGHETDEN RAKVEITPNS PRAEATLGGF GSLGI                   45

SEQ ID NO: 3            moltype = AA  length = 45
FEATURE                 Location/Qualifiers
source                  1..45
                        mol_type = protein
                        organism = Zika virus
SEQUENCE: 3
HGSQHSGMIV NDTGHETDEN RAKVEITPNS PRAEATLGGF GSIGL                   45

SEQ ID NO: 4            moltype = AA  length = 46
FEATURE                 Location/Qualifiers
source                  1..46
                        mol_type = protein
                        organism = Zika virus
SEQUENCE: 4
VHGSQHSGMI VNDTGHETDE NRAKVEITPN SPRAEATLGG FGSLGL                  46
```

```
SEQ ID NO: 5              moltype = AA   length = 47
FEATURE                   Location/Qualifiers
source                    1..47
                          mol_type = protein
                          organism = Zika virus
SEQUENCE: 5
SVHGSQHSGM IVNDTGHETD ENRAKVEITP NSPRAEATLG GFGSLGL                          47

SEQ ID NO: 6              moltype = AA   length = 51
FEATURE                   Location/Qualifiers
source                    1..51
                          mol_type = protein
                          organism = Zika virus
SEQUENCE: 6
RIMLSVHGSQ HSGMIVNDTG HETDENRAKV EITPNSPRAE ATLGGFGSLG L                     51

SEQ ID NO: 7              moltype = AA   length = 53
FEATURE                   Location/Qualifiers
source                    1..53
                          mol_type = protein
                          organism = Zika virus
SEQUENCE: 7
EYRIMLSVHG SQHSGMIVND TGHETDENRA KVEITPNSPR AEATLGGFGS LGL                   53

SEQ ID NO: 8              moltype = AA   length = 46
FEATURE                   Location/Qualifiers
source                    1..46
                          mol_type = protein
                          organism = Zika virus
SEQUENCE: 8
HGSQHSGMIV NDTGHETDEN RAKVEITPNS PRAEATLGGF GSLGLD                           46

SEQ ID NO: 9              moltype = AA   length = 48
FEATURE                   Location/Qualifiers
source                    1..48
                          mol_type = protein
                          organism = Zika virus
SEQUENCE: 9
HGSQHSGMIV NDTGHETDEN RAKVEITPNS PRAEATLGGF GSLGLDCE                         48

SEQ ID NO: 10             moltype = AA   length = 50
FEATURE                   Location/Qualifiers
source                    1..50
                          mol_type = protein
                          organism = Zika virus
SEQUENCE: 10
HGSQHSGMIV NDTGHETDEN RAKVEITPNS PRAEATLGGF GSLGLDCEPR                       50

SEQ ID NO: 11             moltype = DNA   length = 17
FEATURE                   Location/Qualifiers
source                    1..17
                          mol_type = other DNA
                          organism = synthetic construct
SEQUENCE: 11
ccgctgccca acacaag                                                           17

SEQ ID NO: 12             moltype = DNA   length = 24
FEATURE                   Location/Qualifiers
source                    1..24
                          mol_type = other DNA
                          organism = synthetic construct
SEQUENCE: 12
ccactaacgt tcttttgcag acat                                                   24

SEQ ID NO: 13             moltype = DNA   length = 20
FEATURE                   Location/Qualifiers
source                    1..20
                          mol_type = other DNA
                          organism = synthetic construct
SEQUENCE: 13
ttctacaatg agctgcgtgt                                                        20

SEQ ID NO: 14             moltype = DNA   length = 20
FEATURE                   Location/Qualifiers
source                    1..20
                          mol_type = other DNA
                          organism = synthetic construct
SEQUENCE: 14
```

```
gccagacagc actgtgttgg                                                    20

SEQ ID NO: 15              moltype = DNA  length = 19
FEATURE                    Location/Qualifiers
source                     1..19
                           mol_type = other DNA
                           organism = synthetic construct
SEQUENCE: 15
gaaggtgaag gtcggagta                                                     19

SEQ ID NO: 16              moltype = DNA  length = 20
FEATURE                    Location/Qualifiers
source                     1..20
                           mol_type = other DNA
                           organism = synthetic construct
SEQUENCE: 16
gaagatggtg atgggatttc                                                    20

SEQ ID NO: 17              moltype = DNA  length = 31
FEATURE                    Location/Qualifiers
source                     1..31
                           mol_type = other DNA
                           organism = synthetic construct
SEQUENCE: 17
agcctacctt gacaagcaat cagacactca a                                       31

SEQ ID NO: 18              moltype = DNA  length = 20
FEATURE                    Location/Qualifiers
source                     1..20
                           mol_type = other DNA
                           organism = synthetic construct
SEQUENCE: 18
caagcttccc gttctcagcc                                                    20

SEQ ID NO: 19              moltype = AA  length = 20
FEATURE                    Location/Qualifiers
source                     1..20
                           mol_type = protein
                           organism = synthetic construct
SEQUENCE: 19
GMIVNDTGHE TDENRAKVEI                                                    20

SEQ ID NO: 20              moltype = AA  length = 17
FEATURE                    Location/Qualifiers
source                     1..17
                           mol_type = protein
                           organism = Homo sapiens
SEQUENCE: 20
QTLNILVDTG SSNFAVG                                                       17
```

METHODS OF TREATING ALZHEIMERS DISEASE

CROSS-REFERENCE TO RELATED APPLICATIONS

This application is a Divisional of U.S. patent application Ser. No. 17/369,681 filed on Jul. 7, 2021, which claims the benefit of U.S. Patent Application No. 63/049,039 filed on Jul. 7, 2020. The disclosure of the prior applications are considered part of (and are incorporated by reference in) the disclosure of this application.

SEQUENCE LISTING

This application contains a Sequence Listing that has been submitted electronically as an XML file named 24742-0121002_SL_ST26.xml. The XML file, created on Dec. 21, 2023, is 20,480 bytes in size. The material in the XML file is hereby incorporated by reference in its entirety.

TECHNICAL FIELD

This document relates to methods and materials for treating a mammal having Alzheimer's disease (AD). For example, one or more Zika virus (ZIKV) polypeptides can be administered to a mammal having, or at risk of developing, AD to treat the mammal.

BACKGROUND

Alzheimer's disease (AD), one of the top 10 leading causes of death in the United States, is a progressive disease that typically begins with mild memory loss and can lead to loss of the ability to carry on a conversation and respond to the environment affecting a person's ability to carry out daily activities (Xu et al., 2010 *National vital statistics reports* 58(19)). As of 2014, as many as 5 million Americans were living with AD, and the number of people with AD is expected to nearly triple to 14 million people by 2060 (Matthews et al., 201, *Alzheimer's & Dementia* 15:17-24). The costs of treating AD currently fall between $159 and $215 billion, and are projected to rise (Hurd et al., 2013 *NEJM* 368(14):1326-34).

SUMMARY

AD is characterized by the accumulation of the β-amyloid peptide (AB) within the brains. The physiological generation of the Aβ peptide from amyloid precursor protein (APP) is the crucial step in the development of AD. APP is a transmembrane protein expressed at high levels in the brain and metabolized in a rapid and highly complex fashion.

This document provides methods and materials for treating a mammal having AD. For example, one or more ZIKV polypeptides can be administered to a mammal having, or at risk of developing, AD to treat the mammal. As demonstrated herein, APP and ZIKV can physically interact, ZIKV infection can enhance expression of APP polypeptides in both mouse brain cells as well as human mature neurons, APP polypeptides can inhibit ZIKV replication in vivo in mice, as well as in human neuronal stem cells/progenitor cells (NSC/NPC) in vitro. Also as demonstrated herein, select ZIKV polypeptides can reduce or eliminate cleavage of an APP polypeptide. Accordingly, ZIKV polypeptides can be used to treat mammals having, or at risk of developing, AD.

In general, one aspect of this document features methods for treating a mammal having AD. The methods can include, or consist essentially of, administering to a mammal having AD a polypeptide comprising, consisting essentially of, or consisting of the amino acid sequence set forth in SEQ ID NO:1. The mammal can be a human. The mammal can have been identified as having AD. The can be effective to reduce or eliminate a symptom of AD. The symptom of AD can be mental decline, difficulty thinking and understanding, confusion in the evening hours, delusion, disorientation, forgetfulness, making things up, mental confusion, difficulty concentrating, inability to create new memories, inability to do simple math, inability to recognize common things, aggression, agitation, difficulty with self care, irritability, meaningless repetition of own words, personality changes, restlessness, lack of restraint, wandering and getting lost, anger, apathy, general discontent, loneliness, mood swings, depression, hallucination, paranoia, inability to combine muscle movements, jumbled speech, loss of appetite, or any combinations thereof. The method can be effective to increase a level of APP polypeptides within the mammal. The polypeptide can be administered intraperitoneally, intravenously, intramuscularly, or subcutaneously.

In another aspect, this document features methods for increasing a level of APP polypeptides within a mammal having AD. The methods can include, or consist essentially of, administering to a mammal having AD a polypeptide comprising, consisting essentially of, or consisting of the amino acid sequence set forth in SEQ ID NO:1. The mammal can be a human. The mammal can have been identified as having AD. The polypeptide can be administered intraperitoneally, intravenously, intramuscularly, or subcutaneously.

In another aspect, this document features methods for reducing Aβ-amyloid plaque formation within a mammal having AD. The methods can include, or consist essentially of, administering to a mammal having AD a polypeptide comprising, consisting essentially of, or consisting of the amino acid sequence set forth in SEQ ID NO:1. The mammal can be a human. The mammal can have been identified as have AD. The polypeptide can be administered intraperitoneally, intravenously, intramuscularly, or subcutaneously.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1K: ZIKV and APP interact with each other. FIG. 1A. Structural alignment of ZIKV E and BACE1 is as shown. The structure of ZIKV E protein is shown in grey and blue color while the structure of BACE1 is shown in light pink and magenta. The blue part in ZIKV E protein and magenta part in BACE1 are the best aligned parts, which are two β strands with a loop. The aligned structures are around APP binding site. The APP binding site of BACE1 is indicated by a big arrow. FIG. 1B. The best aligned structural parts on ZIKV E protein (blue) and on BACE1 (magenta), are displayed separately. FIG. 1C. The corresponding sequence alignment between the strand sheets on ZIKV E protein (SEQ ID NO:7) and BACE1 protein (SEQ ID NO:20) are displayed with corresponding color background. Red font: the amino acid sequence used for generating P2 peptide. Loop region and sequence in P2 that is not present in the FIG. 1B are also indicated. FIG. 1D. HEK293 cells were transfected with vector (pcDNA3) or APP expression plasmids (pCAX FLAG APP or F-APP). One day later, cells were incubated with ZIKV (PRVABC59) at 0.5 multiplicity of infection (MOI) in 37° C. for one hour. Cells were vigorously washed to remove unadsorbed virus. RNA were isolated from the cells. Same amounts of cDNAs were used for semi-quantitative PCR analyses. Primers for ZIKV and actin were added in separate tubes as shown on the top and amplified with different cycles based previous experiments for linear ranges of amplifications. A 8% polyacrylamide gel was used to separate the PCR products. Standard double-stranded DNA fragment markers are shown on the left in base pairs (bp). Relative ZIKV RNA level (ZIKV/Actin) is as shown on the bottom. FIG. 1E. Three independent experiments were done as in FIG. 1D, and relative ZIKV RNA levels (ZIKV/Actin) in vector and APP-transfected cells were quantified and compared. Student t tests were done. * p<0.05. FIG. 1F. pCAX FLAG APP or pCAX-APP695 were transfected into HEK293 cells and expression of human APP was determined by Western Blot. pcDNA3 was used as a vector control. Molecular weight markers are shown on the left in kilodalton (kDa). FIG. 1G. HEK293 cells were transfected with target plasmids. Cells were incubated with ZIKV and BBS1 scFv expressing or corresponding helper phages simultaneously at 37° C. for one hour. The cells were washed, and RNA were isolated for qRT-PCR assays. Three biological replicates were done and the relative ZIKV/GAPDH amounts were calculated using $2^{-\Delta\Delta Ct}$ method. FIG. 1H. Cortical cortexes from aging mouse brains were dissected and passed through 70 μm and 40 μm cell strainers. Cells were washed and $5\times10^6$ cell clumps/ml were seeded and incubated with various amounts of ZIKV (pfu/ml) at 37° C. for one hour. Supernatants were collected and used for qRT-PCR assays. Total three mice (>1-year-old) were used for the experiments. C57BL/6J(wt): solid bar; two APP-null mice: dashed and open bars respectively. Student t tests were performed, * p<0.05;  p<0.01; * p<0.001. FIG. 1I. Equal volumes of explant cultures were collected and protein expression in cultured cells was examined by Western blot analyses. The identity of proteins is as shown. Results represent two independent experiments from four mice. FIG. 1J. The co-immunoprecipitation assays were used to detect the interaction between ZIKV E and APP in HEK cells. The expression plasmids for APP and ZIKV PrM-E were co-transfected into HEK293T cells for experiment #1. For experiment #2, the cells were transfected with vector (pCDNA3) or APP expression plasmid and infected with recombinant adenovirus expressing ZIKV-PrM-E, or GFP protein. Each experiment was repeated at least three times. Cell lysates were immunoprecipitated with ZIKV E antibody followed by Western blot with APP antibody. The input cell lysates (exp #2) are also shown (bottom panel). The images in the same box indicate they were derived from the same lysates. FIG. 1K. HEK293 cells were transfected with PrM-E and APP695 expression plasmids. One day later, the cells were stained with rabbit ZIKV E and mouse APP antibodies followed by secondary antibodies conjugated with Alexa Fluor 488 and 647 respectively. The cells were examined under a confocal microscope. ZIKV E (green), APP (red), overlay of ZIKV E, APP and nuclei (blue) are shown. Amplified regions and scale bars are also shown.

FIG. 2A. HEK293 cells were transfected with human APP695 expression plasmid, pCAX-APP695, or vector control. Cells were infected with or without ZIKV at 1 MOI overnight. Western blots were used for detection of APP and Tubulin simultaneously. FIG. 2B. Relative levels of APP proteins (APP/Tubulin) in HEK293 cells are shown from three independent experiments. Student t tests were performed, * p<0.05. FIG. 2C. HEK293 cells were transfected with APP695, split into several smaller wells 4-6 hours later. After overnight culture, the cells were treated with cycloheximide (CHX), or CHX plus ZIKV simultaneously for various of times. Cells were collected at indicated times (hours post treatment). Expression of APP and tubulin, determined by Western blots, is as shown. FIG. 2D. Relative levels of APP proteins (APP/Tubulin) in HEK293 cells with or without ZIKV infection are shown. The data are the combinations of two independent experiments (one is shown in FIG. 2C). Solid line: ZIKV infected; dashed line: no ZIKV infection. FIG. 2E. The mixture of human mature cortical neurons was infected with ZIKV (10 MOI) for six hours, and expression of APP and tubulin was determined by Western Blots. One representative result is as shown. FIG. 2F. Relative levels of APP proteins (APP/Tubulin) in human mature neurons are shown from three independent experiments in two batches of human neurons as in FIG. 2E. Student t tests were performed, * p<0.05. FIG. 2G. The mixture of human mature cortical neurons was infected with or without ZIKV (approximate 10 MOI) for one hour, and then cells were treated with CHX for indicated times (minutes). The expression of APP proteins from two independent experiments is as shown. The relative APP expression levels (APP/Tubulin) are indicated in the bottom. FIG. 2H. Mouse brains (WT, C57BL/6J) were dissected from euthanized mice. Mixture of cells were isolated and infected with ZIKV for six hours. The approximate MOI is shown in parenthesis. The relative APP expression levels are indicated in the bottom. i. HEK293 cells were co-transfected with APP695 expression plasmid (0.5 μg) and P2 peptide or BSA protein (1 μg each) with PULSin reagents. One day later, the expression of APP and tubulin were examined by Western Blot analyses. One representative result is as shown. FIG. 2J. Relative APP protein expression levels were calculated from three independent experiments and are as shown. Student t tests were performed, * p<0.05. FIG. 2K. HEK293 cells were co-transfected with APP expression plasmid (0.5 μg) plus BSA (1 μg) or APP (0.2 μg) plus P2 peptide (1 μg) with PULSin reagents. Four hours later, the cells were split into two wells. One day later, the cells were treated with CHX for one hour and lysates were collected. The expression of APP and tubulin were examined. The relative expression of APP proteins is as shown at the bottom.

FIGS. 3A-3E: APP inhibits ZIKV replication. FIG. 3A. Lentivirus expressing siRNA for APP (siAPP) and its scramble lentivirus (siScramble) were used to infect human NPCs/NSCs overnight at 1 MOI. Cells were washed and infected with ZIKV (1 MOI) and one hour later, the media were replaced with fresh media. Two days later, cell media were collected and subjected to real time qRT-PCR analyses. Four independent experiments were done and the relative ZIKV genomic RNA contents in the media were calculated with $2^{-\Delta\Delta Ct}$ method. Student t tests were performed,  p<0.01. FIG. 3B. Human NPCs/NSCs were treated with the siRNA expressing lentivirus and one day later, the cells were collected for Western blot analyses. The identity of target proteins is as shown. FIG. 3C. human NPCs were incubated with ZIKV (1 MOI) in the presence with either BBS1Ab scFv expressing or helper phages (1 transforming unit per cell) for one hour at 37° C. Uninfected viruses were removed and cells were washed with fresh media. Two days later, cell media were subjected to qRT-PCR analysis. Four independent experiments were done and relative ZIKV RNAs in media were calculated with $2^{-\Delta\Delta Ct}$ method. Student t tests were performed,  p<0.01. FIG. 3D. C57BL/6 (WT) and APP-null P4 baby mice were used for intracranially (i.c.) injections of ZIKV (PRVABC59; 1.5×10^4 pfu) or same volumes of 1×PBS. Pink: ZIKV infected neonates; Blue: PBS control mice; Solid line: APP-null neonates; Dashed line: WT mice. The survival of the baby mice was monitored for four days. To compare the survival curves for ZIKV-infected cases of APP-null and WT, the Log-Rank test was applied and the p value is as shown. FIG. 3E. Two strains of mice were i.c. injected with ZIKV. P4 mice: 1×10^3 pfu, n=10 wt, n=11app−/−; P7 mice: 1.5×10^4 pfu, n=9 wt, n=9app−/−; P28 mice: 5×10^4 pfu, n=10 wt, n=11app−/−. The mice with i.c. injected with 1×PBS were controls. Multiple ages and strains were clustered (n=7). Relative levels of ZIKV plus SEM are as shown. Student t tests were performed, * p<0.05; *** p<0.001.

FIGS. 5A-5D: FIG. 5A. pCAX-APP695 or pcDNA3 plasmids were transfected into HEK293 cells and ZIKV attachment assays were done as in FIG. 1D. Real-time quantitative RT-PCR assays (qRT-PCR) were used for measurement of ZIKV RNA, with GAPDH RNA as internal control. The $2^{-\Delta\Delta Ct}$ method was used for calculation for relative RNA levels. Relative ZIKV attachments is as shown. FIG. 5B. Standard curve of the real-time RT-PCR for ZIKV RNA. FIG. 5C. Left panel: cloning strategy for scFv from BBS1 antibody. Right Panel: Binding of Phage BBS1 scFv to BACE1 cleavage site peptide. A 96 well plate was coated with MAP-[ISEVKMDA]8 (peptide representing the BACE1 cleavage site on APP), washed twice with PBST (0.05% Tween20) (PBS #02-023-5A, BI; Tween-20 #P1379 Sigma-Aldrich) and blocked with 5% slim milk O/N at 4° C. Different phage concentration in equal volume were added to the plate and allowed to bind for one hour at 37° C. followed by 3 washes with PBST. Next, Rabbit anti-phage polyclonal antibodies (#PA1-26758 Invitrogen) were added at 1:5000 and allowed to bind for 1 h at 37° C. followed by 3 washes with PBST. For detection, goat anti-rabbit HRP conjugated (#AP307P Sigma-Aldrich) at 1:10,000 and allowed to bind for 1 h at 37° C. followed by 3 washes with PBST. The assay was developed using OPD substrate. FIG. 5D. Essentially same experiments were done as in FIG. 1h. Cortical cortexes from aged mouse brains (>1-year-old) were used to isolate cell clumps and 5×10^6 cell clumps/ml were seeded and infected with various amounts of ZIKV at 37° C. for one hour. In the FIG. 1h, ZIKV stocks were propagated in Vero cells and the virus used here were propagated in Huh7.5 cells. Supernatants were collected and used for qRT-PCR assays. Total three mice were used for the experiments. C57BL/6J(wt): solid bar; two APP-null mice: dashed and open bars respectively. Student t tests were performed, * p<0.05;  p<0.01; * p<0.001.

FIG. 6A. HEK293 cells were transfected with EBV LMP1 expression plasmid or vector control (pcDNA3). One day later, the cells were infected with or without ZIKV overnight as in FIG. 2a. Western blots were used for detection of LMP1 and tubulin simultaneously. The images in the same box indicate they were derived from the same gels. The identity of the proteins is as shown. FIG. 6B. HEK293 cells were co-transfected with different amounts of LMP1 expression plasmid and P2 peptide, or BSA protein (1 g each) with PULSin reagents. One day later, the expression of APP and tubulin were examined simultaneously by Western Blot analyses. The identity of the proteins is as shown.

FIG. 7A) Nonamyloidogenic processing of APP involving α-secretase followed by γ-secretase. FIG. 7B) Amyloidogenic processing of APP involving cellular β-site amyloid precursor protein cleaving enzyme 1 (BACE1) followed by γ-secretase. Both processes generate soluble ectodomains (sAPPα and sAPPβ) and intracellular C-terminal fragments (AICD). Potential ZIKV binding site is indicated.

FIG. 9A. Both APP-null (B6.129S7-Apptm1Dbo/J) and STAT2-null mice (B6.129-Stat2tm1Shnd/J) were obtained from The Jackson laboratory. Two strains were crossed and F1 intercrossing were done. F2 mice were screened for desired double knockout genotype (app−/−; stat2−/−). The DKO strain was first confirmed by genetic analyses (data not shown), and then tissues were collected for Western blot analyses (brains for detection of APP, and splenocytes for STAT2 respectively). WT represents C57BL/6J, also from the Jackson Laboratory. FIG. 9B. A DKO mouse was infected with ZIKV (PRV-ABC59; 1×10^6 pfu) for 8 days and a swelling liver was identified. FIG. 9C. Two DKO mice were infected with ZIKV (PRVABC59; 1×10^6 pfu) and one with PBS. One ZIKV-infected mouse was dead at dpi 10, and another ZIKV-infected one was paralyzed. PBS control mouse was normal. The mice were euthanized and dark (black) intestine was observed in the ZIKV infected individual (bottom mouse). The PBS control mouse was normal (top mouse). We also dissected the dead ZIKV-infected mouse, dark intestine also observed (not shown).

FIG. 12A. DKO dams are mated with heterozygous (app+/−; stat2−/−) sires. ZIKV are used to infect pregnant dams and infection mode is determined in Example 3. Possible genotypes of the fetuses are shown. FIG. 12B. Pregnant dams are infected with ZIKV. Days for infection (red) and collection (blue) are shown. Total 24 dams are needed.

DETAILED DESCRIPTION

Figure 1H:
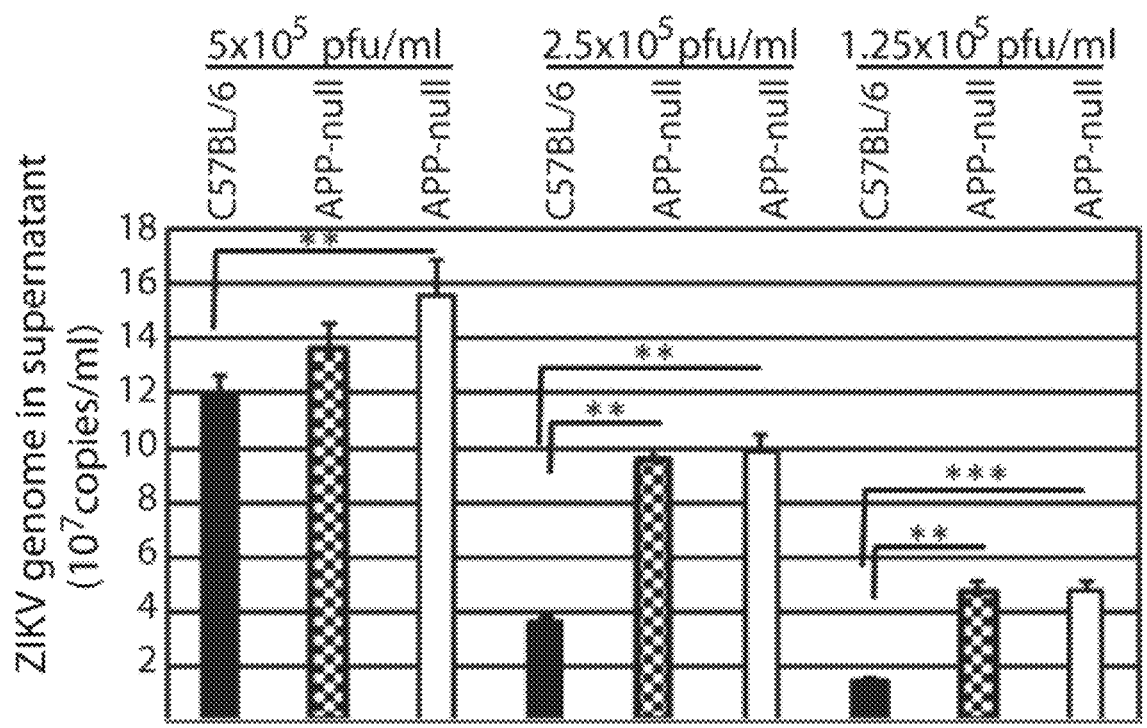

This document provides methods and materials for treating a mammal having AD. For example, one or more ZIKV polypeptides (e.g., one or more ZIKV polypeptides having the ability to reduce or eliminate cleavage of an APP polypeptide) can be administered to a mammal having, or at risk of developing, AD to treat the mammal.

Any appropriate mammal (e.g., a mammal having, or at risk of developing, AD) can be treated as described herein. Examples of mammals that can have AD and can be treated as described herein (e.g., by administering one or more ZIKV polypeptides to the mammal) include, without limitation, humans, non-human primates (e.g., monkeys), dogs, cats, mice, rats, sheep, goats, bears, cheetahs, and dolphins.

In some cases, methods described herein can include identifying a mammal (e.g., a human) as having AD. Any appropriate method can be used to identify a mammal as having AD. For example, physical and neurological examinations (e.g., to assess reflexes, muscle tone and strength, ability to get up from a chair and walk across the room, sense of sight and hearing, coordination, and balance), mental status testing (e.g., to test your thinking (cognitive) and memory skills, neuropsychological tests, laboratory tests (e.g., to rule out other disorders that can cause some symptoms similar to those of AD, such as a thyroid disorder or vitamin B-12 deficiency), cerebrospinal fluid (CSF) tests, electroencephalography (EEG), and/or imaging tests (e.g., brain-imaging tests such as magnetic resonance imaging (MRI), computerized tomography (CT), and/or positron emission tomography (PET) to evaluate loss (degeneration) of brain cells and/or to rule out other causes such as hemorrhages, brain tumors or strokes) can be used to identify a mammal (e.g., a human) as having AD.

When treating a mammal (e.g., a human) having, or at risk of developing, AD as described herein (e.g., by administering one or more ZIKV polypeptides to the mammal), the ZIKV polypeptide can be any ZIKV polypeptide. In some cases, a ZIKV polypeptide provided herein can reduce or eliminate cleavage of an APP polypeptide. A ZIKV polypeptide can be a full-length ZIKV polypeptide or a fragment of a ZIKV polypeptide provided that the fragment has the ability to reduce or eliminate cleavage of an APP polypeptide (e.g., a biologically active fragment). A ZIKV polypeptide can be from (e.g., can be derived from) any lineage of ZIKV. A ZIKV polypeptide can be a synthetic polypeptide. A ZIKV polypeptide can be from any clade of ZIKV. A ZIKV polypeptide can be any strain of ZIKV. Examples of ZIKVs that a ZIKV polypeptide can be derived from include, without limitation, East African ZIKV, West African ZIKV, Asian ZIKV, and South American ZIKV.

A ZIKV polypeptide provided herein (e.g., a ZIKV polypeptide that can reduce or eliminate cleavage of an APP polypeptide) can comprise, consist essentially of, or consist of the amino acid sequence set forth in SEQ ID NO:1.

SEQ ID NO: 1
HGSQHSGMIVNDTGHETDENRAKVEITPNSPRAEATLGGFGSLGL

In some cases, a ZIKV polypeptide provided herein can be a substantially pure polypeptide. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel. In some cases, a substantially pure polypeptide provided herein can be a polypeptide that is synthesized to have a purity of at least about 60, 65, 70, 75, 80, 85, 90, 95, or 99 percent.

In some cases, a ZIKV polypeptide provided herein that consists essentially of the amino acid sequence set forth in SEQ ID NO:1 can be a polypeptide that has zero, one, or two amino acid substitutions within the articulated sequence of SEQ ID NO:1, has zero, one, two, three, four, or five amino acid residues preceding the articulated sequence of SEQ ID NO:1, and/or has zero, one, two, three, four, or five amino acid residues following the articulated sequence of SEQ ID NO: 1, provided that the ZIKV polypeptide can reduce or eliminate cleavage of an APP polypeptide. Examples of ZIKV polypeptides that consist essentially of the amino acid sequence set forth in SEQ ID NO: 1 are set forth in Table 1.

TABLE 1

| Exemplary ZIK V polypeptides. | |
|---|---|
| Polypeptide Sequence | SEQ ID NO: |
| HGSQHSGMIVNDTGHETDENRAKVEITPNSPRAEATLGGFGSLGI | 2 |
| HGSQHSGMIVNDTGHETDENRAKVEITPNSPRAEATLGGFGSIGL | 3 |
| VHGSQHSGMIVNDTGHETDENRAKVEITPNSPRAEATLGGFGSLGL | 4 |
| SVHGSQHSGMIVNDTGHETDENRAKVEITPNSPRAEATLGGFGSLGL | 5 |
| RIMLSVHGSQHSGMIVNDTGHETDENRAKVEITPNSPRAEATLGGFGSLGL | 6 |
| EYRIMLSVHGSQHSGMIVNDTGHETDENRAKVEITPNSPRAEATLGGFGSLGL | 7 |
| HGSQHSGMIVNDTGHETDENRAKVEITPNSPRAEATLGGFGSLGLD | 8 |
| HGSQHSGMIVNDTGHETDENRAKVEITPNSPRAEATLGGFGSLGLDCE | 9 |
| HGSQHSGMIVNDTGHETDENRAKVEITPNSPRAEATLGGFGSLGLDCEPR | 10 |

A polypeptide provided herein (e.g., a ZIKV polypeptide that comprises, consists essentially of, or consists of the amino acid sequence set forth in SEQ ID NO: 1) can be any appropriate length. For example, a polypeptide provided herein can be from 35 amino acid residues to 55 amino acid residues (e.g., from 35 amino acid residues to 52 amino acid residues, from 35 amino acid residues to 50 amino acid residues, from 35 amino acid residues to 47 amino acid residues, from 35 amino acid residues to 45 amino acid residues, from 38 amino acid residues to 55 amino acid residues, from 40 amino acid residues to 55 amino acid residues, from 42 amino acid residues to 55 amino acid residues, from 37 amino acid residues to 53 amino acid residues, from 40 amino acid residues to 50 amino acid residues, from 38 amino acid residues to 42 amino acid residues, from 40 amino acid residues to 48 amino acid residues, or from 43 amino acid residues to 50 amino acid residues) in length.

When treating a mammal having, or at risk of developing, AD, one or more ZIKV polypeptides (e.g., one or more ZIKV polypeptides having the ability to reduce or eliminate cleavage of an APP polypeptide) can be administered to the mammal at any appropriate time. For example, one or more ZIKV polypeptides can be administered to a mammal having, or at risk of developing, AD before, during (e.g., concurrent with), and/or after the mammal exhibits one or more symptoms of AD. In some cases, one or more ZIKV polypeptides can be administered to a mammal before the mammal exhibits one or more symptoms of AD (e.g., when the mammal is asymptomatic and/or prior to AD developing). In some cases, one or more ZIKV polypeptides can be administered to a mammal after the mammal exhibits one or more symptoms of AD.

One or more ZIKV polypeptides (e.g., one or more ZIKV polypeptides having the ability to reduce or eliminate cleavage of an APP polypeptide) can be administered to a mammal in need thereof (e.g., a mammal having, or at risk of developing, AD) by any appropriate route. Administration can be local or systemic. Examples of routes of administration include, without limitation, intraperitoneal, intravenous, intramuscular, subcutaneous, oral, intranasal, inhalation, transdermal, and parenteral administration.

When treating a mammal having, or at risk of developing, AD, the treatment can include the administration of a therapeutically effective amount of one or more ZIKV polypeptides (e.g., one or more ZIKV polypeptides having the ability to reduce or eliminate cleavage of an APP polypeptide). The terms "effective amount" and "therapeutically effective amount" refer to that amount of one or more ZIKV polypeptides sufficient to result in a therapeutic effect.

In some cases, treating a mammal having, or at risk of developing, AD as described herein (e.g., by administering one or more ZIKV polypeptides to the mammal) can be effective to reduce the severity of the AD and/or to reduce or eliminate one or more symptoms of the AD. In some cases, a symptom can be a cognitive symptom. In some cases, a symptom can be a behavioral symptom. In some cases, a symptom can be a mood symptom. In some cases, a symptom can be a psychological symptom. Examples of symptoms of AD can include, without limitation, mental decline, difficulty thinking and understanding, confusion in the evening hours, delusion, disorientation, forgetfulness, making things up, mental confusion, difficulty concentrating, inability to create new memories, inability to do simple math, inability to recognize common things, aggression, agitation, difficulty with self-care, irritability, meaningless repetition of own words, personality changes, restlessness, lack of restraint, wandering and getting lost, anger, apathy, general discontent, loneliness, mood swings, depression, hallucination, paranoia, inability to combine muscle movements, jumbled speech, and loss of appetite. In some cases, a symptom of AD can be as described elsewhere (see, e.g., cdc.gov/aging/aginginfo/alzheimers.htm#How; and mayoclinic.org/diseases-conditions/alzheimers-disease/symptoms-causes/syc-20350447). For example, one or more ZIKV polypeptides can be administered to a mammal in need thereof (e.g., a human having, or at risk for developing, AD) as described herein to reduce one or more symptoms of AD within the mammal by, for example, 10, 20, 30, 40, 50, 60, 70, 80, 90, 95, or more percent.

In some cases, treating a mammal having, or at risk of developing, AD as described herein (e.g., by administering one or more ZIKV polypeptides to the mammal) can be effective to reduce or eliminate AB-amyloid plaque formation within the mammal. For example, one or more ZIKV polypeptides can be administered to a mammal in need thereof (e.g., a human having, or at risk for developing, AD) as described herein to reduce Aβ-amyloid plaque formation within the mammal by, for example, 10, 20, 30, 40, 50, 60, 70, 80, 90, 95, or more percent.

In some cases, treating a mammal having, or at risk of developing, AD as described herein (e.g., by administering one or more ZIK V polypeptides to the mammal) can be effective to increase expression of an APP polypeptide within a mammal having, or at risk for developing, AD (e.g., resulting in an increased level of APP polypeptides within the mammal). The term "increased level" as used herein with respect to a level of an APP polypeptide in a mammal having, or at risk for developing, AD refers to any level that is greater than the level of that APP polypeptide observed in that mammal prior to being treated as described herein. In some cases, an increased level of an APP polypeptide can be a level that is at least 5 percent (e.g., at least 10, at least 15, at least 20, at least 25, at least 35, at least 50, at least 75, at least 100, or at least 150 percent) higher than the level of that APP polypeptide prior to being treated as described herein. In some cases, when samples have an undetectable level of an APP polypeptide prior to treatment as described herein, an increased level can be any detectable level of an APP polypeptide. It will be appreciated that levels from comparable samples are used when determining whether or not a particular level is an increased level. For example, one or more ZIKV polypeptides can be administered to a mammal in need thereof (e.g., a human having, or at risk for developing, AD) as described herein to reduce increase expression of an APP polypeptide within the mammal by, for example, 10, 20, 30, 40, 50, 60, 70, 80, 90, 95, or more percent. Any appropriate method can be used to determine whether or not a level of APP polypeptides has been increased. For example, quantitative RT-PCR (RT-qPCR), western blotting, and/or ELISAs can be used to determine whether or not level of APP polypeptides has been increased.

In some cases, one or more ZIKV polypeptides can be administered to a mammal having, or at risk of developing, AD in the absence of any carriers (e.g., additives, fillers, vehicles, and/or diluents).

In some cases, one or more ZIKV polypeptides can be formulated into a composition (e.g., a pharmaceutically acceptable composition) for administration to a mammal having, or at risk of developing, AD. For example, one or more ZIKV polypeptides can be formulated together with one or more pharmaceutically acceptable carriers (e.g., additives, fillers, vehicles, and/or diluents). In some cases, pharmaceutically acceptable carrier can be non-naturally occurring. Pharmaceutical acceptable carriers that can be used in a pharmaceutical composition described herein include, without limitation, dextrose, methanol, dimethyl sulfoxide (DMSO), ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and wool fat.

In some cases, a composition including one or more ZIKV polypeptides to be administered to a mammal (e.g., a human) in need thereof (e.g., a mammal having, or at risk of developing, AD) can include one or more ZIKV polypeptides as the sole active ingredient used to treat AD.

In some cases, a composition including one or more ZIKV polypeptides to be administered to a mammal (e.g., a human) in need thereof (e.g., a mammal having, or at risk of developing, AD) can include one or more ZIKV polypeptides together with one or more additional active ingredients (e.g., active ingredients that can be used to treat a mammal having, or at risk of developing, AD). Examples of additional active ingredients that can be used to treat a mammal having, or at risk of developing, AD include, without limitation, cholinesterase inhibitors (e.g., donepezil, galantamine, and rivastigmine), and memantine.

A composition including one or more ZIKV polypeptides can be designed for any route of administration. For example, a composition including one or more ZIKV polypeptides can be designed for parenteral (e.g., intraperitoneal) administration. Compositions suitable for parenteral administration include, without limitation, aqueous and non-aqueous sterile injection solutions that can contain anti-oxidants, buffers, bacteriostats, and solutes that render the formulation isotonic with the blood of the intended recipient. For example, a composition including one or more ZIKV polypeptides can be designed for oral administration. Compositions suitable for oral administration include, without limitation, liquids, tablets, capsules, pills, powders, gels, and granules.

A composition including one or more ZIKV polypeptides can be administered to a mammal (e.g., a human) in need thereof (e.g., a mammal having, or at risk of developing, AD) in any appropriate amount (e.g., any appropriate dose). An effective amount of a composition including one or more ZIKV polypeptides can be any amount that reduces the severity and/or reduces or eliminates one or more symptoms of AD without producing significant toxicity to the mammal. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and level of severity of the AD may require an increase or decrease in the actual effective amount administered.

A composition including one or more ZIKV polypeptides can be administered to a mammal (e.g., a human) in need thereof (e.g., a mammal having, or at risk of developing, AD) in any appropriate frequency. The frequency of administration can be any frequency that reduces the severity of the AD and/or reduces or eliminates one or more symptoms of the AD without producing significant toxicity to the mammal. For example, the frequency of administration can be from about once a day to about ten times a day, from about three times a day to about eight times a day, or from about four times a day to about six times a day. The frequency of administration can remain constant or can be variable during the duration of treatment. As with the effective amount, various factors can influence the actual frequency of administration used for a particular application. For example, the effective amount, duration of treatment, use of multiple treatment agents, route of administration, and level of severity of the AD may require an increase or decrease in administration frequency.

A composition including one or more ZIKV polypeptides can be administered to a mammal (e.g., a human) in need thereof (e.g., a mammal having, or at risk of developing, AD) for any appropriate duration. An effective duration for administering a composition including one or more ZIKV polypeptides can be any duration that reduces the severity of the AD and/or reduces or eliminates one or more symptoms of the AD without producing significant toxicity to the mammal. For example, the effective duration can vary from several days to several months or years to a lifetime. In some cases, the effective duration for the treatment of mammal in need thereof can range in duration from about 2 days to about a week. Multiple factors can influence the actual effective duration used for a particular treatment. For example, an effective duration can vary with the frequency of administration, effective amount, use of multiple treatment agents, route of administration, and level of severity of the AD.

In some cases, methods described herein also can include administering to a mammal in need thereof (e.g., a mammal having, or at risk of developing, AD) one or more additional treatments used to treat a mammal having, or at risk of developing, AD. Examples of additional active ingredients that can be used to treat a mammal having, or at risk of developing, AD include, without limitation, cholinesterase inhibitors (e.g., donepezil, galantamine, and rivastigmine), and memantine. In cases where a mammal having, or at risk of developing, AD is treated with one or more non-nucleoside ZIKV polypeptides and is treated with one or more additional agents used to treat AD, the additional treatment used to treat AD can be administered at the same time or independently. For example, when administered independently, the one or more ZIKV polypeptides can be administered first, and the one or more additional treatment used to treat AD can be administered second, or vice versa.

In certain instances, a course of treatment and the severity of one or more symptoms related to the condition being treated (e.g., AD) can be monitored. Any appropriate method can be used to determine whether or not the severity of one or more symptoms is reduced or eliminated. For example, the severity of a ZIKV infection can be assessed using any appropriate methods and/or techniques and can be assessed at different time points. For example, physical and neurological examinations (e.g., to assess reflexes, muscle tone and strength, ability to get up from a chair and walk across the room, sense of sight and hearing, coordination, and balance), mental status testing (e.g., to test your thinking (cognitive) and memory skills, neuropsychological tests, laboratory tests (e.g., to rule out other disorders that can cause some symptoms similar to those of AD, such as a thyroid disorder or vitamin B-12 deficiency), CSF tests, EEG, and/or imaging tests (e.g., brain-imaging tests such as MRI, CT, and/or PET to evaluate loss (degeneration) of brain cells and/or to rule out other causes such as hemorrhages, brain tumors or strokes) can be used to determine the severity of one or more symptoms of a ZIKV infection.

In some cases, one or more ZIKV polypeptides can be used to treat a mammal having a disease or disorder associated with increased levels of Aβ polypeptides and/or decreased levels of APP polypeptides. Examples of diseases and disorders associated with increased levels of Aβ polypeptides and/or decreased levels of APP polypeptides include, without limitation, cerebral amyloid angiopathy.

The invention will be further described in the following examples, which do not limit the scope of the invention described in the claims.

EXAMPLES

Example 1: APP is a Restriction Factor for ZIKV in the Brains

Results
ZIKV Interacts with APP Protein

Using information about the ZIKV virion structure, we applied protein structure alignment methods, such as SSM and TM-alignment, to screen structurally homologous proteins with known binding partners to ZIKV virion and E protein. The binding partners were considered as potential ZIKV binding candidates. Dendritic Cell-Specific Intercellular adhesionmolecule-3-Grabbing Non-integrin (DC-SIGN) (also known as cluster of differentiation 209) is one of the cellular receptors for ZIKV. This method predicted that ZIKV E protein interacted with members of the C-type lectin receptor family 4, including DC-SIGN (data not shown).

Beta-secretase 1 (BACE1) was a hit of the screening, and there were some structural similarities between BACE1 and ZIKV virion, particularly within the ZIKV E protein. BACE1 is a transmembrane protein that binds to and cleaves APP proteins. PDB IDs for structures of ZIKV E and BACE1, obtained from the PDB Bank (rcsb.org/), are 5IRE chain A and 3HW1 chain A, respectively. Alignments of the ZIKV E and BACE1 had shown only limited structural similarities between the two proteins: both proteins have a similar β-hairpin structure, a 2-stranded β-sheets (FIG. 1A, 1B). Interestingly, the corresponding part in BACE1 was located in the binding region to APP (FIG. 1A). Amino acid residues, GSS, form a very short loop region in the β-hairpin of BACE1. In contrast, ZIKAV E has a longer corresponding part (FIG. 1C). Because APP is a target of BACE1, the similarity in the structures suggested that APP protein might be a potential candidate for ZIKV binding.

To examine whether APP was related to ZIKV infection, human embryonic kidney fibroblast 293 cells (HEK293) were used for two reasons: 1) the cells are not susceptible for ZIKV infection; and 2) the cells have very low levels of endogenous APP. First, we tested whether APP was a factor for ZIKV attachment to cells. N-terminal FLAG-tagged full-length APP expression plasmids were transfected into the HEK293 cells, and one day later, the transfected cells were mixed with ZIKV for one hour. The cells were washed extensively to remove the unbound viruses. The attachments of ZIKV to transfected cells were examined by semi-quantitative reverse transcription polymerase chain reaction (RT-PCR).

Figure 1I:
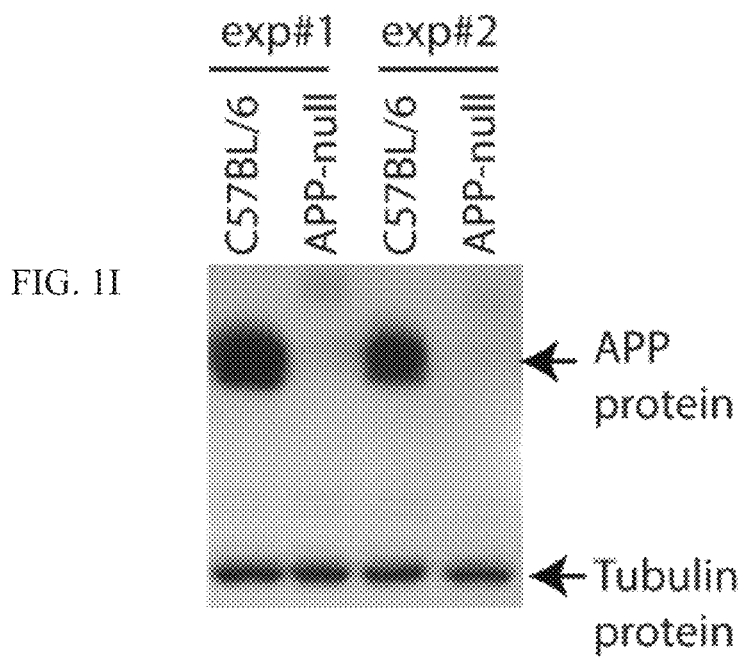
Figure 1J:
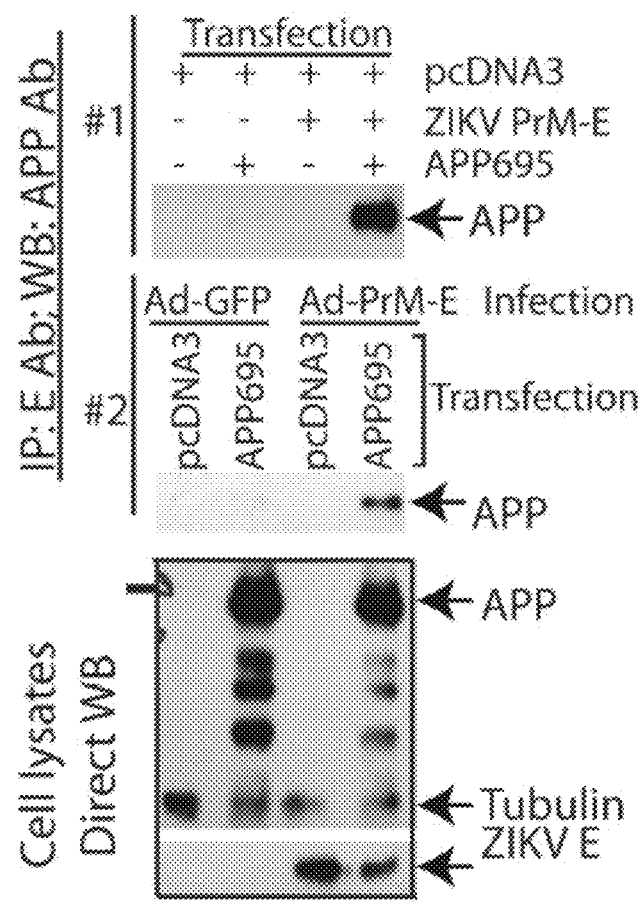
Figure 1K:
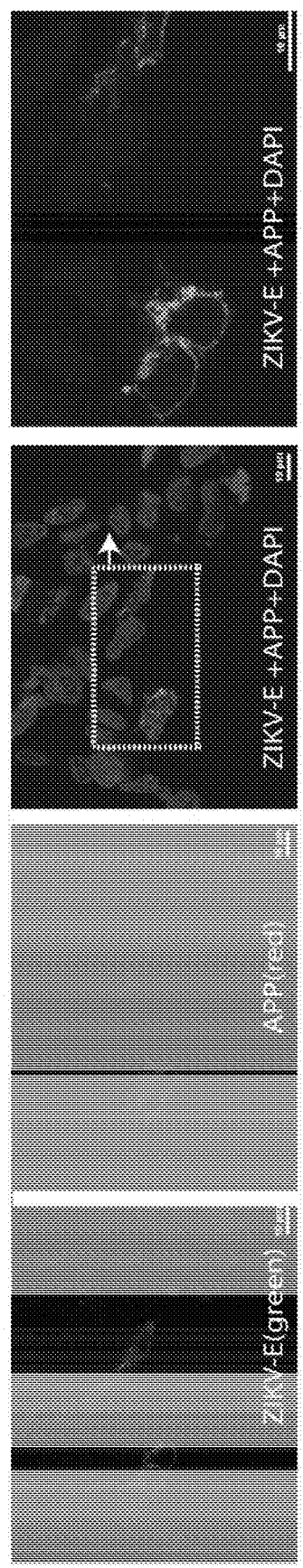
Figure 5A:
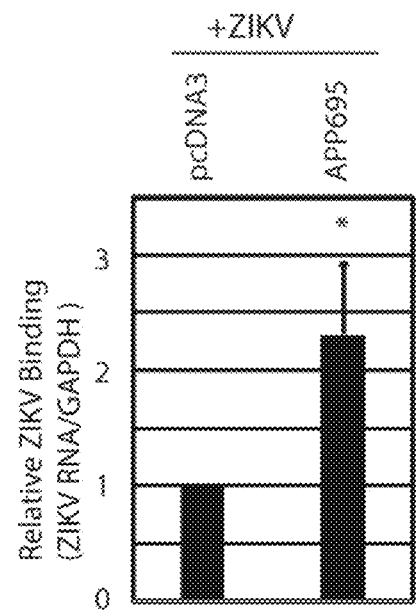
Figure 5B:
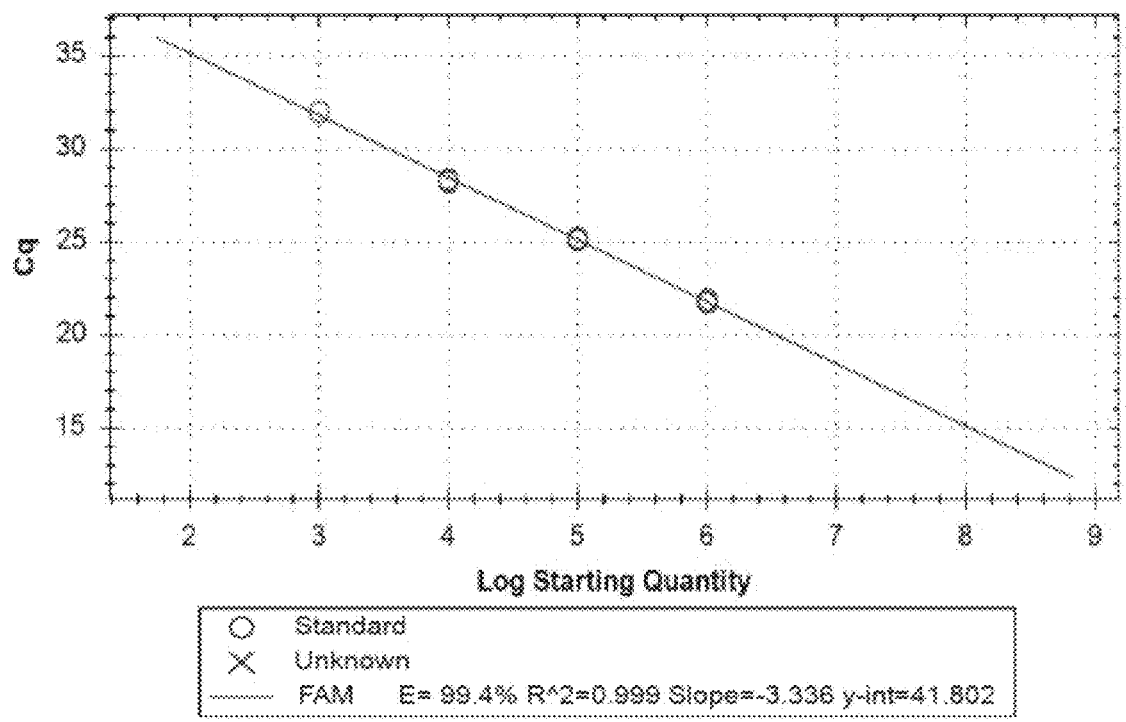

ZIKV bound to APP-expressing cells more strongly than the control vector-transfected HEK293 cells (FIGS. 1D, and 1E). Of note, incubating viruses and cells for a short period of time and measuring viral components are a common approach for assessing viral attachment to cells. To avoid the potential interference from N-terminal inserted FLAG-tag, an APP695 expression plasmid without any tags, was used for ZIKV binding assays with quantitative real time RT-PCR (qRT-PCR) assays. APP695 is the predominant form of APP in the brains and more ZIKV could attach to APP695-expressing cells (FIGS. 5A, 5B). The expression of APP was confirmed by various methods and appeared to be located in the cytoplasm and possibly cell membranes (FIGS. 1F, 1K).

BBS1 antibody targets the BACE1 cleavage site of APP. Because ZIKV may bind to a similar site based on molecular structural analyses (FIG. 1A), we tested if BBS1 Ab could interfere with ZIKV attachments to cells. The single-chain variable fragment (scFv) of the BBS1 antibody was cloned and expressed in a phage, and the BBS1 scFv phage was able to bind to the target peptide (FIG. 5C). The BBS1 scFv expressing phages and its control helper phages were incubated with ZIKV for attachment assays to APP695 expressing HEK293 cells. The BBS1 scFv phages inhibited ZIKV attachments to APP695 expressing cells (FIG. 1G). The results suggested that the ZIKV might specifically bind to APP and the region of the binding was located around the BACE1 cleavage site (FIG. 1A).

Figure 5D:
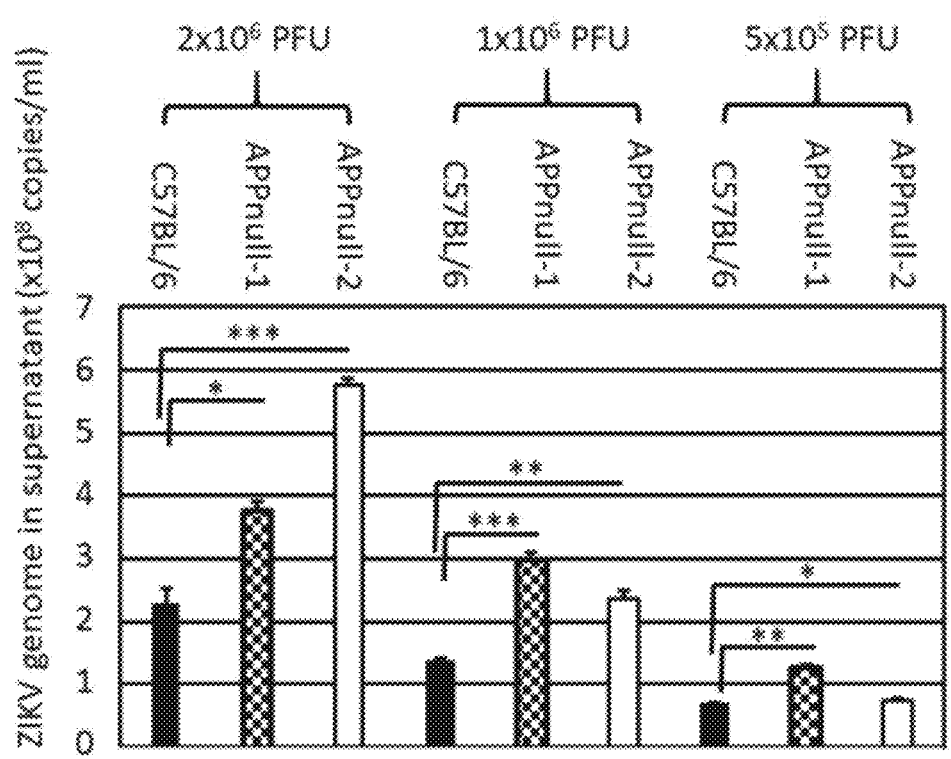

Adult brains seem to be more resistant to ZIKV infection. One possible explanation is that adult brains have very few or no NPCs/NSCs. We suspected that adult brain cells, with the expression of APP, might trap ZIKV and thus protected NPCs/NSCs or other infectable cells from ZIKV infection. To test the hypothesis, cortical cortexes from aging (>1-year-old) APP-null (B6.129S7-Apptm1Dbo/J) and age-matched control wild type mice (WT, C57BL/6J) were isolated and passed through cell strainers (see Methods for details). The same amounts of cell clumps were dispensed and immediately incubated with ZIKV for one hour, and the amounts of free viruses remaining in the media were determined as a measure of viral absorptions to brain cortexes. Culture media from explant APP-null brain cortexes had higher levels of ZIKV viral genomes than those in WT mice, suggesting that ZIKV was being trapped by APP protein (FIG. 1H, FIG. 5D). Other than similar cell clumps, similar levels of tubulin were detected in the two batches of explant cortex cultures, and the genotype status of APP-null strain was also verified at the same time (FIG. 1I). Those results suggested that mature brain cells with APP could bind to and trap ZIKV.

ZIKV E protein is considered as the major virion protein for attachment to host cells. Interestingly, PrM-E complex has been shown to be a good candidate for ZIKV vaccine, which suggested that PrM may help E protein to generate the correct conformation for interaction with host proteins. To test the potential interaction of ZIKV-APP further, we employed co-immunoprecipitation assay (co-IP) for potential ZIKV and APP interactions. By co-transfection of PrM-E and APP expression plasmids in HEK293 cells, a ZIKV-E antibody immunoprecipitated APP proteins in transfected cell lysates (FIG. 1J; experiment #1). Of note the experiment #2 was done by transfection of APP695 and infection with a recombinant adenovirus expressing ZIKV PrM-E proteins, and similar results were obtained. Unfortunately, with multiple APP antibodies and extensive efforts, we could not use APP antibody to precipitate ZIKV E protein in the same or similar co-IP conditions for an unknown reason (data not shown).

To confirm the co-IP results, whether ZIKV E and APP proteins were co-localized in the same cells was examined. As shown in FIG. 1K, ZIKV-E and APP were partially co-localized in the same transfected cells (FIG. 1K). In the majority (>90%) of APP and ZIKV E co-expressing cells, partial co-localization patterns of the two proteins were observed. All those data collectively suggest that ZIKV has a physical interaction with APP protein.

ZIKV Enhances APP Protein Expression

Figure 2A:
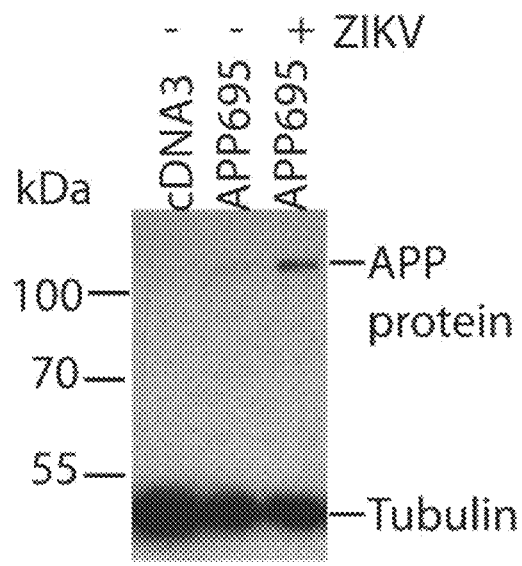
FIGS. 2A-2K: ZIKV stabilizes APP proteins.
Figure 2B:
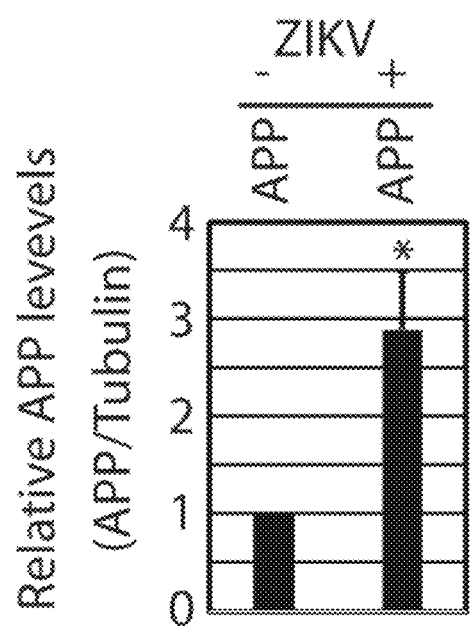
Figure 2C:
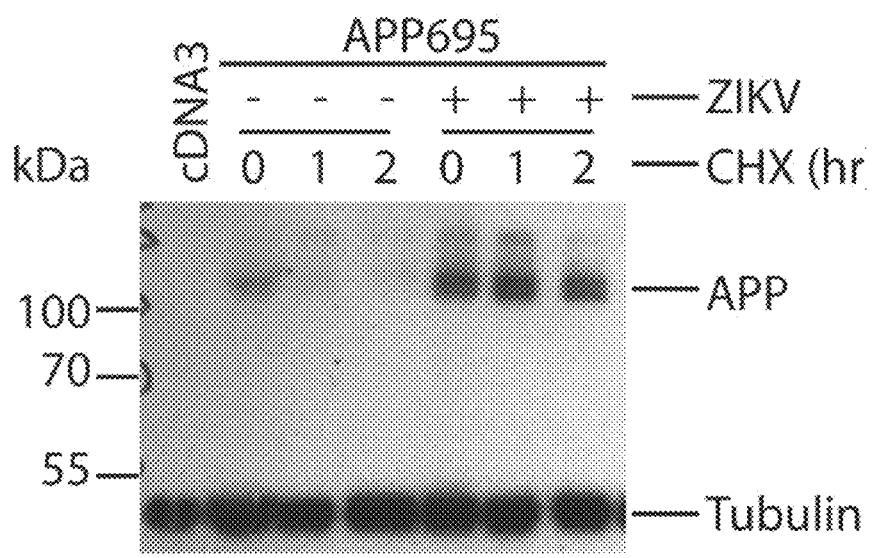
Figure 2D:
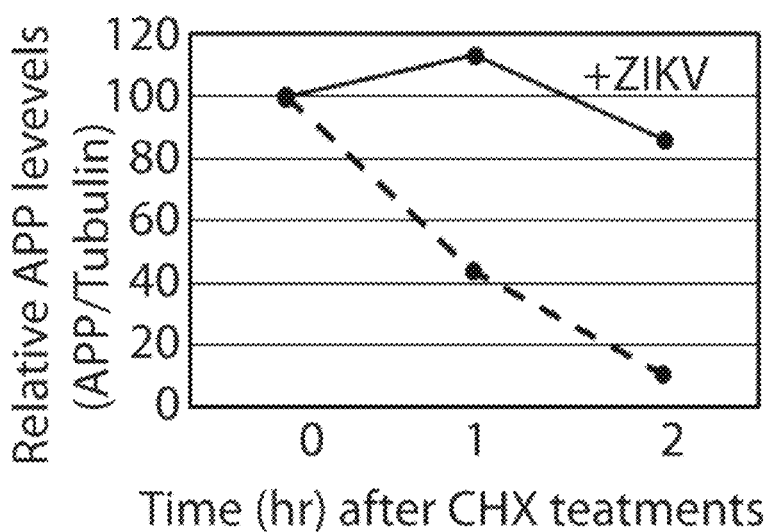
Figure 2E:
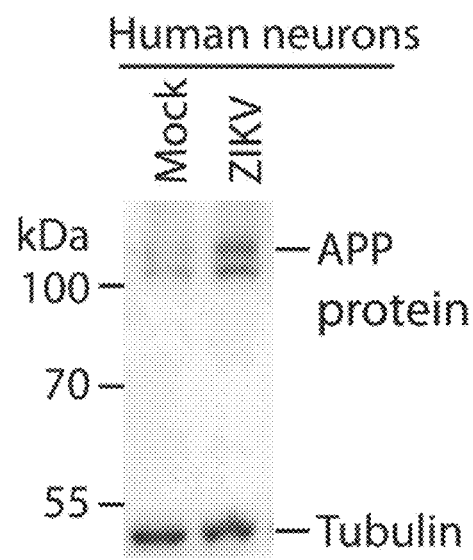
Figure 2F:
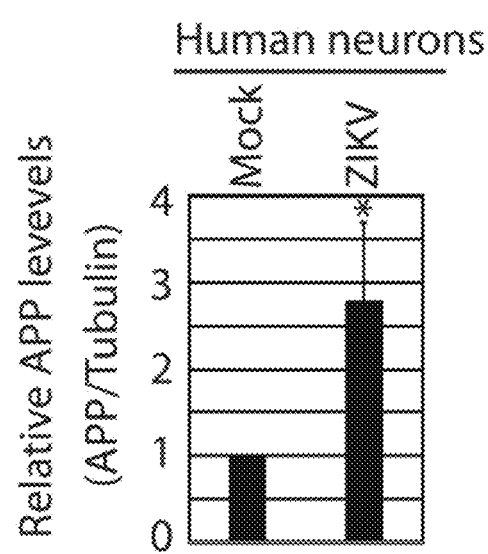
Figure 2G:
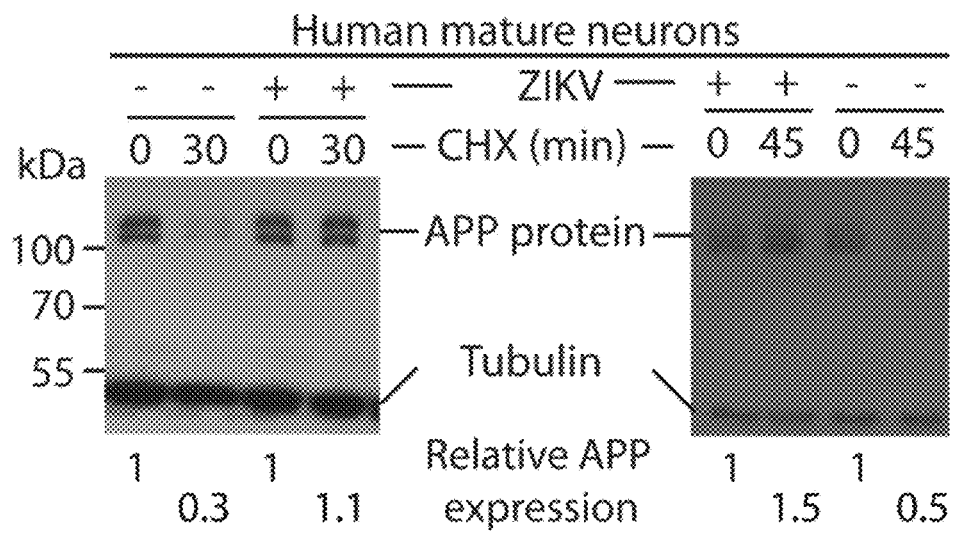
Figure 2H:
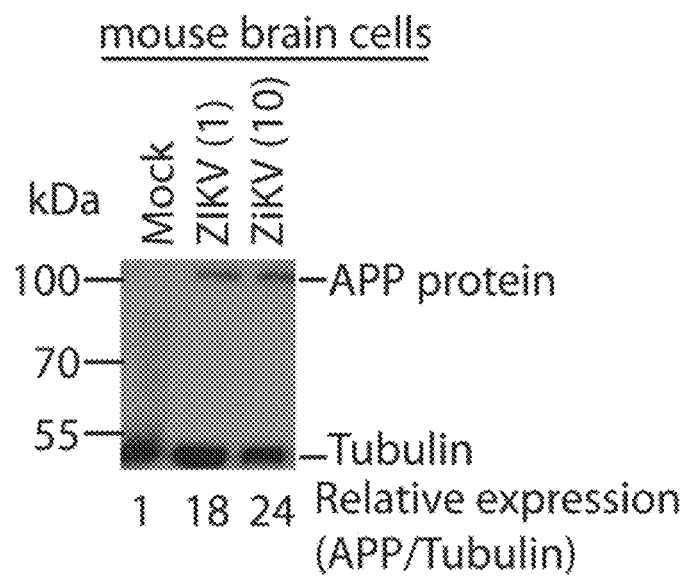
Figure 6A:
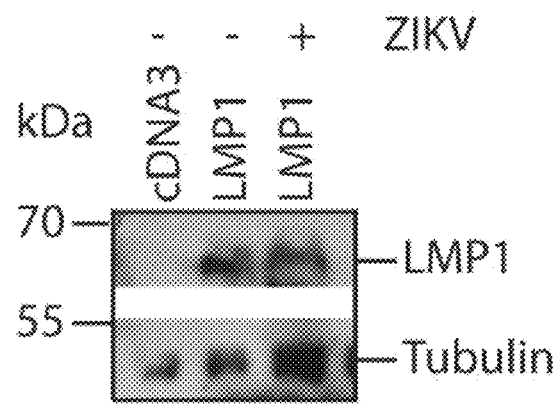
FIGS. 6A-6B.

APP is quickly metabolized through an orderly process by multiple proteases. Whether ZIKV binding affected APP expression was examined. HEK293 cells were transfected with APP expressing plasmids and the cells were incubated with ZIKV overnight. APP-expressing cells exposed to ZIKV exhibited elevated levels of the APP protein than those non-exposed cells (FIGS. 2A and 2B). It is interesting to note that the overexpression of transfected APP diminished the induction effects, suggesting that the expression of APP in a cell might have an upper limit (data not shown). Moreover, the induction by ZIKV was specific for APP protein because Epstein-Barr virus latent membrane protein 1 (LMP1) could not be enhanced by ZIKV infection (FIG. 6A). LMP1 is a membrane protein, partially located in endosome, and considered as a constitutively active receptor. To examine the mechanistic bases for the increase in APP protein in these cells with ZIKV, a protein synthesis inhibitor, cycloheximide (CHX), was added to the culture media. The half-life of APP protein in the presence of ZIKV was increased significantly, suggesting that ZIKV-attachments increased the stability of APP protein in these cells (FIGS. 2C and 2D). As NPCs/NSCs are major targets for ZIKV replication, we chose mature neurons to test if ZIKV attachments could enhance APP expression to avoid the complications from viral entry/replication. A mixture of human cortical neurons derived from human embryonic stem cells was infected with ZIKV for six hours, and higher expression of APP was observed (FIGS. 2E and 2F). In addition, the increases might be due to the increase of protein half-life (FIG. 2G). Whether in vivo infection of ZIKV would cause the accumulation of APP in mice were also examined. However, due to the variability of APP in different individual mice (see FIG. 1I for a reference), no conclusive results could be obtained with whole brain protein analyses (data not shown). An explant infection system was established whereby the mixtures of whole mouse brain cells were isolated and incubated with ZIKV. Mouse brain cells had a higher APP protein expression after six hours of incubation with ZIKV (FIG. 2H). APP levels also increased after 24 hours ZIKV infection (data not shown). Of note the endogenous mouse APP levels might determine the levels of inductions: the lower endogenous APP levels lead to higher induction by ZIKV.

Figure 2I:
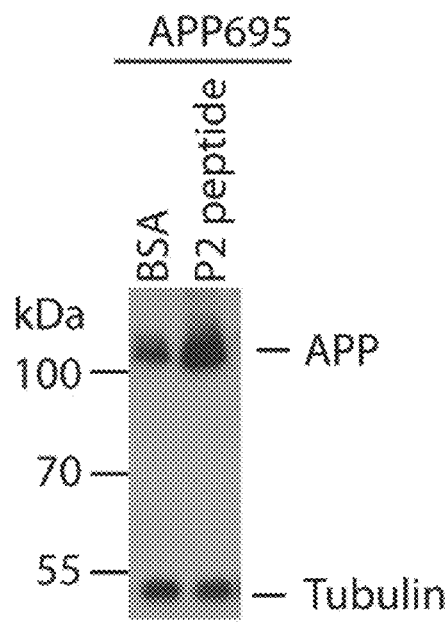
Figure 2J:
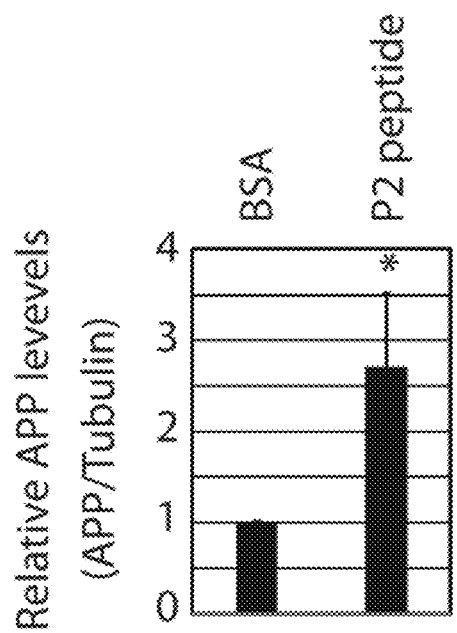
Figure 2K:
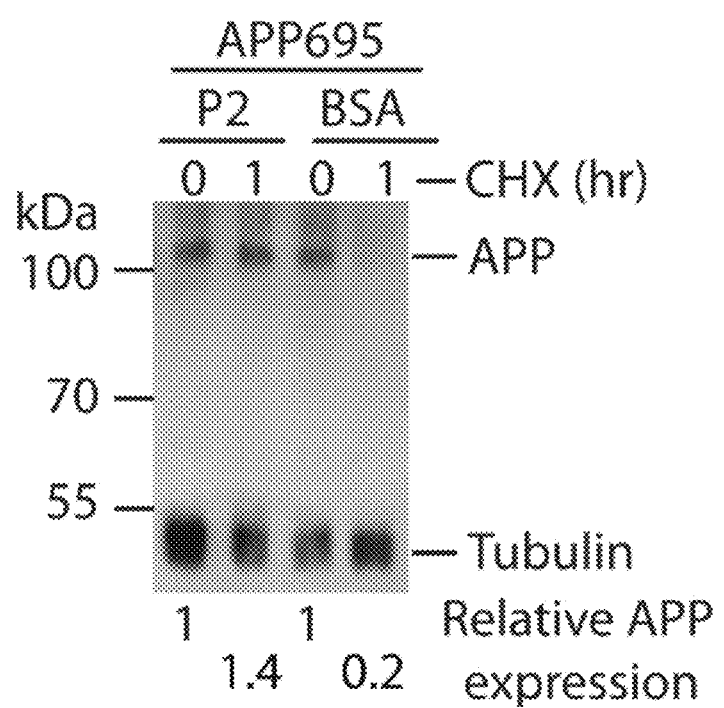
Figure 6B:
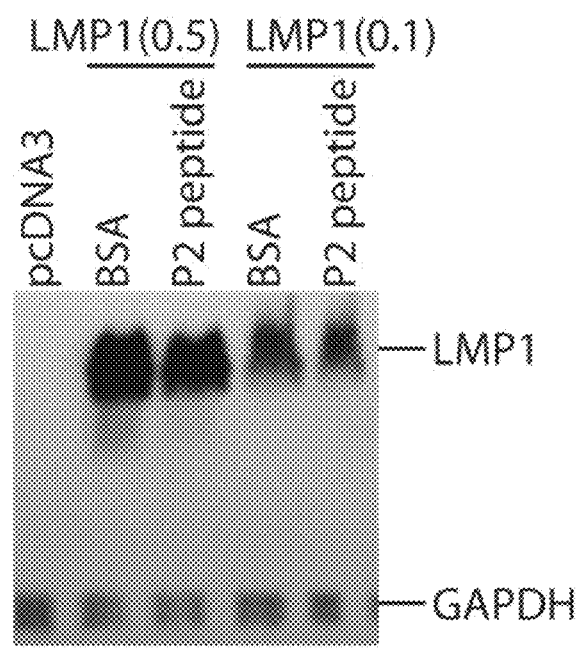

We suspected that the loop in the specific structure of ZIKV E protein was responsible for the potential interaction with APP (FIGS. 1A and 1B). A peptide (P2) derived from the potential binding site, the β-hairpin region, was synthesized with sequence optimization (FIG. 1C). Located in the core region of the ZIKV E protein and being hydrophobic, the eight amino acid stretch, EYRIMLSV, in the β-hairpin region of E protein was not included in the P2 sequence. Furthermore, the P2 peptide could potentially form a similar structure as in the native protein by including extra amino acids in the C-terminus (FIGS. 1B and 1C). The P2 peptide is a water-soluble molecule but could not enhance APP expression when treating cells directly (data not shown). It is known that the interactions between BACE1 and APP protein happen in both biosynthetic and endocytic compartments inside cells, and ZIKV E protein was predicted to bind targets in the endosomal compartments. Therefore, we transfected P2 peptide into cells to ensure the peptide could meet APP in endocytic compartments physically. The P2 peptide could increase the expression of APP comparing with the BSA control (FIGS. 2I and 2J). Again, the expression of vial LMP1 could not be enhanced by the peptide co-transfection (FIG. 6B). Furthermore, a similar mechanism to ZIKV was established for the peptide-mediated enhancement (FIG. 2K). All these data suggest that ZIKV enhances APP expression at least partially through modulation of the APP protein stability.

APP is a Negative Regulator of ZIKV Replication

Although ZIKV could bind to APP-expressing cells (FIGS. 1D-1H), APP did not facilitate viral replication in HEK293 cells two days after infection as measured by either plaque or qRT-PCR assays (data not shown). Therefore, APP was clearly not a receptor for the virus. Next, the role of APP as a regulator for ZIKV was examined in NPCs/NSCs, a major target of the virus in the brains and do express APP. The human NPCs/NSCs used in the studies were derived from the NIH approved H9 human embryonic stem cells and characterized using standard protocols. Small interfering RNA (siRNA) was used to specifically knockdown gene expressions.

The recombinant lentiviruses expressing APP siRNA were used to infect NPCs/NSCs. The APP-knockdown cells were then infected by ZIKV. The viral replications were monitored by the qRT-PCR two days later. The culture supernatants from APP-knockdown cells had higher viral genomic RNA copies than those from control cells (FIG. 3A). The effectiveness of siRNA expressing lentivirus on APP expression was confirmed by Western blot analyses (FIG. 3B).

The scFv of BBS1 antibody expressing phages could inhibit ZIKV-interactions with APP (FIG. 1G). Whether this interference affected ZIKV replication was examined. The BBS1 expression phages were mixed with ZIKV during viral infection of human NPCs/NSCs. The scFv of BBS1 Ab-treatment led to enhancement of ZIKV replication in human NPCs/NSCs (FIG. 3C).

The Functional Significance of APP in ZIKV Infection In Vivo was Examined in APP-Null Mice.

Figure 3D:
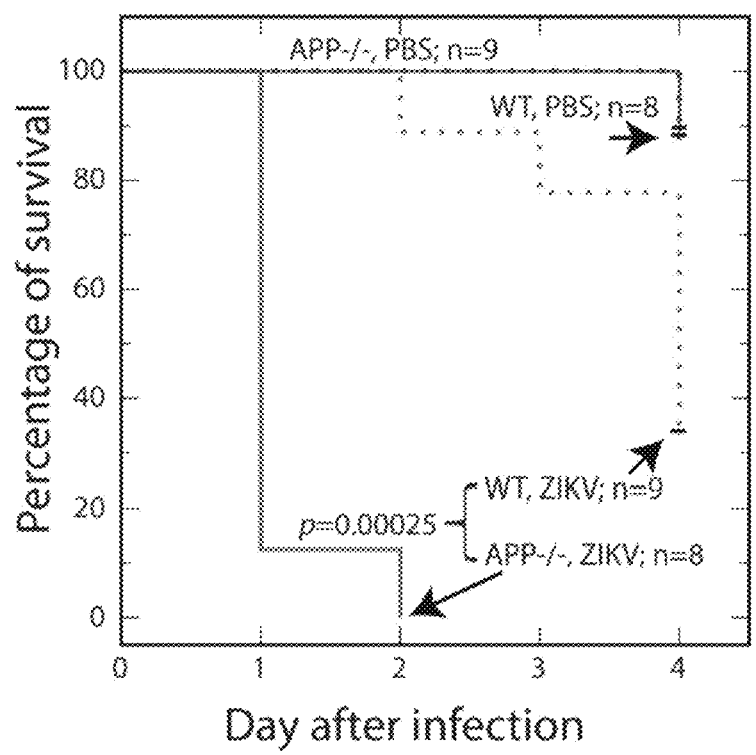
Figure 3E:
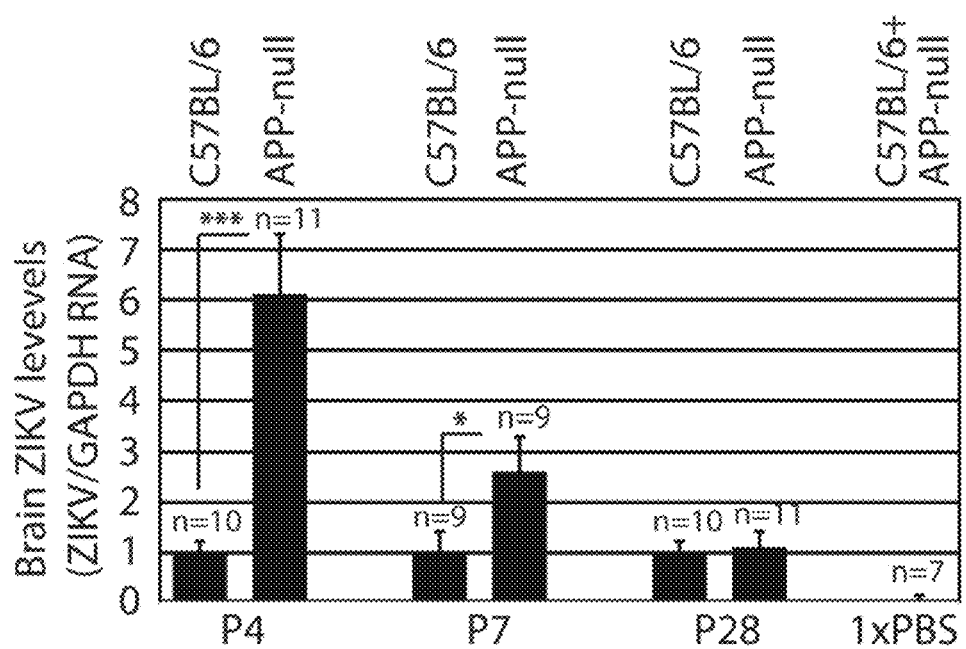

Due to the fact that brains have different NPSs/NSCs proportions in different developmental stages, both neonatal and adult mice were examined for their susceptibility to ZIKV infections. The postnatal day 4 (P4) neonates were injected intracranially (i.c.) with ZIKV ($1.5 \times 10^4$ pfu), and the differences in survival rates between APP-null and WT mice were compared (FIG. 3D). Clearly, APP-null neonates were more sensitive to ZIKV infection than their WT counterparts. Because of the higher mortality in P4 APP-null neonates (FIG. 3D), lower dosages of ZIKV ($1 \times 10^3$ pfu) were chosen for another set of i.c. injections. While all WT mice (10/10) survived, some APP-null neonates (3/14) died two days after ZIKV injection. Whole brains were isolated after euthanasia from surviving neonates and RNA were isolated. Relative levels of ZIKV RNA in the brains were determined by qRT-PCR. APP-null mice had higher viral loads in the brains than WT P4 ones (FIG. 3E).

In P7 neonates, however, the dosage of ZIKV ($1.5 \times 10^4$ pfu) that caused serious neonate death in P4 (FIG. 3E) did not generate much effects on mortality in both APP-null as well as WT mice: all mice survived for two days. In the following viral load detections, APP-null mouse brains had three-fold higher viruses than WT counterparts (FIG. 3E). Interestingly, when we tested the viral replication and mortality in P28 mice, there was no mortality in four days after i.c. injections with the higher ZIKV load, and no differences for viral replication were observed between the two strains of mice (FIG. 3E).

All those data suggest that APP is a negative regulator of ZIKV replication in vitro in human NPCs/NSCs, and in vivo in mouse brains. The inhibitory effects of APP on ZIKV replication seems to be associated with the ages of mice.

Materials and Methods

Mice

C57BL/6J and APP-null mice (app−/−; B6.129S7-Apptm1Dbo/J) mice were purchased from Jackson Laboratories. All mice were bred and housed at the American Association for Accreditation of Laboratory Animal Care-accredited facility under specific-pathogen-free conditions. All experimental protocols were approved by the Institutional Animal Care and Use Committee and followed federal guidelines.

Brain Explant Culture

For cortical cortex culture, aged mice (>1 year old) were euthanized with $CO_2$. The cerebrum was removed after cutting the cranium from the neck to the nose. A midline incision between the hemispheres were performed, and the cortex from the brain were peeled, cut into small pieces (1-2 $mm^3$), and passed through 70 µm cell strainers first, then a 40 µm one subsequently. The cell clumps were washed twice with DMEM plus 10% fetal bovine serum (FBS), counted, and dispensed at desired concentrations. The cells clumps were immediately incubated with ZIKV at 37° C. for one hour for viral absorption study. For whole brain explant culture, cerebrums were isolated and cut into smaller pieces and passed through 70 µm and 40 µm cell strainers. The cell clumps were used directly for ZIKV infections.

ZIKV Infection Study in Mice

Four day old (P4), one week old (P7), and four week old (P28) mice were intracranially (i.c.) injected with 15 µl solutions with 31 G syringes for P4 and P7 mice or 50 µl solutions with 29 G syringes for P28 mice. Hypodermic anesthesia (P4, P7 mice) or isoflurane anesthesia (P28 mice) were used following standard protocol. Animals were observed daily for clinical illness. The brains were collected at 2 day post inoculation (dpi) for P4 and P7 mice, and 4 dpi for P28 mice. RNA were isolated and used for measurement of ZIKV RNA. Mortality was observed for a period of four days.

Cells, Virus, Plasmids and Antibodies

Human embryonic kidney fibroblast 293 (or HEK 293, CRL-1573) and its derivative 293T cells, African green monkey kidney cell line Vero, Human hepatoma cell lines Huh7.5 (gifts from Dr. Padmanabhan), human neuroblastoma cells SH-SY5Y were obtained from the ATCC. The cells were grown and maintained in Dulbecco's modified Eagle's medium (DMEM) containing 10% fetal bovine serum (FBS) and 1× penicillin-streptomycin (PS) in a humidified chamber with 5% $CO_2$ at 37° C.

The Zika virus strain PRVABC59 were obtained from the Centers for Disease Control and Prevention, Fort Collins, Colorado, USA. The virus were prepared in Vero cells or Huh7.5 cells. The stock virus was stored in small aliquots at −80° C. Virus titers were determined by plaque assay on Vero cells. Basically, duplicates of serial 10-fold dilutions of virus were applied to Vero cell monolayers in 24-well plates. The inoculum was removed after one hour incubation, and the cell monolayers were overlaid with medium containing 1% low-gelling-temperature agarose. The cells were fixed in 10% formaldehyde in PBS for 30 min, after 5 days incubation. The agarose plugs were removed, and the cells were stained with 0.1% crystal violet in 30% methanol. Plaques were counted and virus titers were calculated. The pooled human APP siRNA/shRNA/RNAi Lentivirus (siAPP; cat #: iV001195) and its control, Scrambled siRNA GFP Lentivirus (siScramble; cat #: LVP015-G) were both purchased from Applied Biological Materials Inc.

The pCAX FLAG APP (Addgene plasmid #30154) is a FLAG-tagged APP expression plasmid APP and pCAX APP 695 (Addgene plasmid #30137), an expression plasmid for predominant form of APP in the brains. pCI-neo-ZIKV-prME is expression plasmid for PrM-E protein. pcDNA3 (Invitrogen) is a cloning vector used as controls for transfections.

The antibodies for β-amyloid (B-4) (sc-28365), glyceraldehyde-3-phosphate dehydrogenase (0411) (sc-47724), and goat anti-mouse IgG-HRP (sc-2005) were from Santa Cruz. APP C-terminal Ab (Clone C1/6.1; Cat #: 802803) and ZIKV E antibody (GTX133314) were from Biolegend and GeneTex respectively. Donkey anti-Rabbit IgG Secondary Antibody Alexa Fluor 488 conjugate; Cat #A-21206 and Donkey anti-Mouse IgG Secondary Antibody Alexa Fluor 647 conjugate; Cat #A-31571 were both purchased form ThermoFisher Scientific. Tubulin antibody (Cat #: T6557) was purchased from Sigma.

Human Pluripotent Stem Cells (hPSCs) Differentiation into Neural Progenitor Cells (hNPCs) and Mature Cortical Neurons and ZIKV Infection The hPSCs (H9 hESCs) were purchased from WiCell Research Institute (Cat #WA09, WiCell). The hPSCs were maintained in 6-well plate coated with Matrigel (Cat #354277, BD Biosciences) in Essential 8™ medium (E8, Cat #A1517001, Invitrogen). Cells were passaged every 4 days with 0.5 mM EDTA (Cat #AM9260G, Invitrogen). Media were changed daily. Cells were routinely checked for the expression of pluripotency markers, OCT4 (Cat #962649, R&D System) and NANOG (Cat #963488, R&D System), their capability to form teratomas in immunodeficient mice, their karyotypes, bacterial and mycoplasma contaminations. The hPSCs were dissociated with accutase (Cat #A1110501, Life Technologies) and plated in Matrigel-coated 6 well plates ($2\times10^6$ cells/well) and cultured in E8 medium overnight to reach >90% confluency. E8 medium was removed and replaced with neural induction medium consisting of Essential 6™ medium (E6, Cat #A1516401, Invitrogen) supplied with 100 nM LDN193189 (Cat #S2618, Selleckchem) and 10 µM SB431542 (Cat #S1067, Selleckchem) for 11 days. The resulting cells were considered as hNPCs, and their identities were confirmed. The hNPCs were infected with a pooled human APP siRNA/shRNA/RNAi Lentivirus (siAPP; cat #: iV001195) and its control, Scrambled siRNA GFP Lentivirus (siScramble; cat #: LVP015-G; both from Applied Biological Materials Inc.) at 1 MOI overnight, and second day, cells were washed and infected with ZIKV (1 MOI) and one hour later, the media were replaced with fresh media. Two days later, cell media were collected and subjected to real time qRT-PCR assays. For BBS1Ab phage treatments, hNPCs were incubated with ZIKV (1 MOI) in the presence with either BBS1Ab expressing or helper phages (1 transforming unit per cell) for one hour at 37° C. Cells were washed with fresh media the uninfected viruses were removed. Two days later, cell media were subjected to qRT-PCR analysis.

To differentiate hNPCs into the cortical neurons, hNPCs were harvested on day 11 and re-plated to Matrigel-coated 6 well plates, and cultured in neural differentiation medium consisting of Neurobasal® Media (Cat #21103049, Life Technologies), B27 (50×, Cat #17504044, Life Technologies), BDNF (20 ng/ml, Cat #450-02, PeproTech), GDNF (10 ng/ml, Cat #450-10, PeproTech), L-ascorbic acid (200 µM, Cat #NC0602549, Life Technologies), DAPT (2.5 µM, Cat #S2215, Selleckchem), Dibutyryl-CAMP (0.5 mM, Cat #sc-201567A, Santa Cruz Biotechnology) for another 19 days. Half medium was changed every two days. The identities of the mature neurons were Tbr1+(Cat #ab31940, Abcam) and Tuj1+(Cat #T8578, Sigma) dual positive. The cells were infected with ZIKV and treated with CHX as described in the text and Figure legends.

Generation of BBS1 Antibody ScFv Expressing Phages

Total RNA was extracted from BBS2 hybridoma cells using Tri-reagent (#93289 Sigma-Aldrich). The cDNA was synthesized from the total RNA by M-mulV reverse transcriptase (11062603001—Sigma-Aldrich) using oligodT23 primer (O4387—Sigma-Aldrich). The variable domains of the murine light and heavy chains were amplified and sequenced. Based on this, sequence specific primers for BBS2 Vh and Vl were designed harboring the appropriate restriction sites. Next BBS Vh and Vl were cloned into PCC 16 phagemid. First the Vh was cloned using NcoI (#10835315001 Sigma-Aldrich) and BclI restriction (#10693952001 Sigma-Aldrich) sites, followed by Vl cloning based on EcoRI (#10200310001 Sigma-Aldrich) and NotI (#11014714001 Sigma-Aldrich) restriction sites, yielding PCC16-BBS ScFv phagemid. For production, TG1 bacteria (#LUC60502-2 Sigma-Aldrich) containing the PCC16-BBS ScFv phagemid were grown at 37° C. in 10 ml of 2YT medium (#Y2377 Sigma-Aldrich) with 100 µg/ml Amp (#40345717748211 Sigma-Aldrich) up to OD600~0.5, infected with 1:100 M13K07 helper phage (#N0315S-NEB) and incubated for 30 min without shaking followed by 30 min with 100 rpm shaking at 37° C. The infected cells were then grown in IL of 2YT with 100 µg/ml Amp and 70 µg/ml Kan (#60615 Sigma-Aldrich) O/N at 30° C. with 250 rpm shaking. The next day the growing media (containing the phages) was collected and phages were purified by PEG/NaCl (#1546605, S7653 Sigma Aldrich) precipitation twice followed by Cs gradient purification. The biding capacity of the phages was evaluated using ELISA. Phage-BBs ScFv was able to bind MAP peptide representing the BACE cleavage site on APP with high affinity compared to almost no background of Helper phage.

ZIKV Binding Assays

Attractene Transfection Reagent (Cat #: 301007; Qiagen) was used for transfection of 293 or 293T cells. One day later, ZIKV were incubated with the cells for one hour at 37° C. The cells were washed three times with 1×PBS and used for RNA isolation for RT-PCR analyses. For explant cultures, different amounts of viruses were incubated with cortical cortex explant cultures ate 37° C. for one hour. The culture media were centrifuged in an Eppendorf centrifuge at maximum speed for one minute and the supernatants were used to isolate RNA using QIAamp Viral RNA Mini Kit (Cat #: 52904, Qiagen). The equal amounts of RNA solutions Immunofluorescence Staining of Cells 293 cells were transfected with PrM-E and APP695 expression plasmids at 1:1 ratios. Next day the transfected cells were washed once with 1×PBS, fixed with 4% paraformaldehyde (Sigma) for 15 min at room temperature. Cells were permeabilized and blocked with 0.1% Triton X-100 (Sigma) and 0.4% bovine serum albumin (BSA; A7906; Sigma) in PBS for 20 minutes. Samples were then incubated with APP C-terminal Ab (1:200 dilutions) and ZIKV E antibody (1:800 dilutions) for one hour, followed by incubation with secondary antibodies (Donkey anti-Rabbit IgG Secondary Antibody Alexa Fluor 488 conjugate and Donkey anti-Mouse IgG Secondary Antibody Alexa Fluor 647 conjugate) for one more hour at room temperature. Both secondary antibodies were used with 1:1000 dilutions and the dilution buffer for primary and secondary antibodies was 0.1% Tween 20 (Sigma) and 0.4% bovine serum albumin (BSA; A7906; Sigma) in 1×PBS. The samples were then stained with DAPI (4',6-diamidino-2-phenylindole), washed three times with PBS and mounded. All samples were examined a Nikon-Ti2 fluorescence microscope and images were obtained using a Nikon A1r-Ti2 confocal system at the Microscopy Core Facility at the UNL.

Western Blot Analysis with Enhanced Chemiluminescence (ECL)

Separation of proteins on SDS-PAGE was carried out following the standard protocol. After the proteins were transferred to a nitrocellulose or Immobilon membrane, the membrane was blocked with 5% nonfat dry milk in TBST (50 mM Tris-HCl pH 7.5, 200 mM NaCl, 0.05% Tween-20) at room temperature for 30 minutes. It was washed briefly with TBST, and incubated with the primary antibody in 5% milk in TBST for 1 hour at room temperature, or overnight at 4° C. After washing the membrane with TBST three times (10 minutes each), it was incubated with the secondary antibody at room temperature for 1 h. The membrane was then washed three times with TBST, treated with ECL detection reagents, and exposed to BlueBlot™ HS film from Life Science Products (XR-0810-100). The intensities of the target signals were measured by a BioRad ChemiDoc MP Imaging system.

Quantitative Real Time Reverse Transcription Polymerase Chain Reaction (qRT-PCR)

For RNA from brains or cells, TRIzol™ Reagents (Cat #: 15596026; Invitrogen) were used for RNA isolation with standard protocol. For viral RNA in the media, QIAamp Viral RNA Mini Kits (Cat #: 52904; Qiagen) were used following manufacturer's recommendations. SuperScript™ II Reverse Transcriptase (Cat #: 18064014; Invitrogen) were used for first cDNA strand synthesis. Routine methods for semi-quantitative RT-PCR were performed as described. The ZIKV primers were: ZIK-F: 5'-CCG CTG CCC AAC ACA AG-3' (SEQ ID NO:11); ZIK-R: 5'-CCA CTA ACG TTC TTT TGC AGA CAT-3' (SEQ ID NO:12). The human actin primers were: Actin1: 5'-TTC TAC AAT GAG CTG CGT GT-3' (SEQ ID NO:13), and Actin 2: 5'-GCC AGA CAG CAC TGT GTT GG-3' (SEQ ID NO:14). For qRT-PCR, abundance of target RNAs was quantified by CFX96 Real-Time System (BIORAD) or Applied Biosystems Step One plus Real Time PCR system following the manufacturers' recommendations. The ZIKV primers were ZIKA-F and -R. Primers for mouse GAPDH: 5'-GAA GGT GAA GGT CGG AGT A-3 (SEQ ID NO:15)' and 5'-GAA GAT GGT GAT GGG ATT TC-3' (SEQ ID NO:16).

The probes for ZIKV and GAPDH were 5'-AGC CTA CCT TGA CAA GCA ATC AGA CAC TCA A-3 (SEQ ID NO:17)' and 5'-CAA GCT TCC CGT TCT CAG CC-3' (SEQ ID NO:18) respectively. The probes were labelled with 6-carboxyfluorescein phosphoramidite (FAM) reporter dye at the 5' end and 6-carboxytetramethylrhodamine (TAMRA) at the 3' end. The $2^{-\Delta\Delta Ct}$ method was used for calculation of the relative ZIKV expression (ZIKV/GAPDH).

Protein Stability Assays

For transfection of 293 cells, the Attractene Transfection Reagent (Cat #: 301007; Qiagen) was used following manufacturers recommendations. Protein biosynthesis inhibitor, cycloheximide (CHX), was purchased from Sigma (C7698). The cells were treated with CHX (100 µg/ml) with ZIKV simultaneously and cell lysates were made at indicated times and used for Western blot analysis. For mature neurons, the cells were incubated with ZIKV for one hour, and then CHX was added, and cell lysates were collected at indicated times.

Statistical Analysis

General statistical analyses were performed by functions implemented in Microsoft Excel and R. Two group comparisons were done with Student's two-tailed unpaired T-test. The R package of "Survival" was used to fit and plot the survival curves.

Figures 7A, 7B:
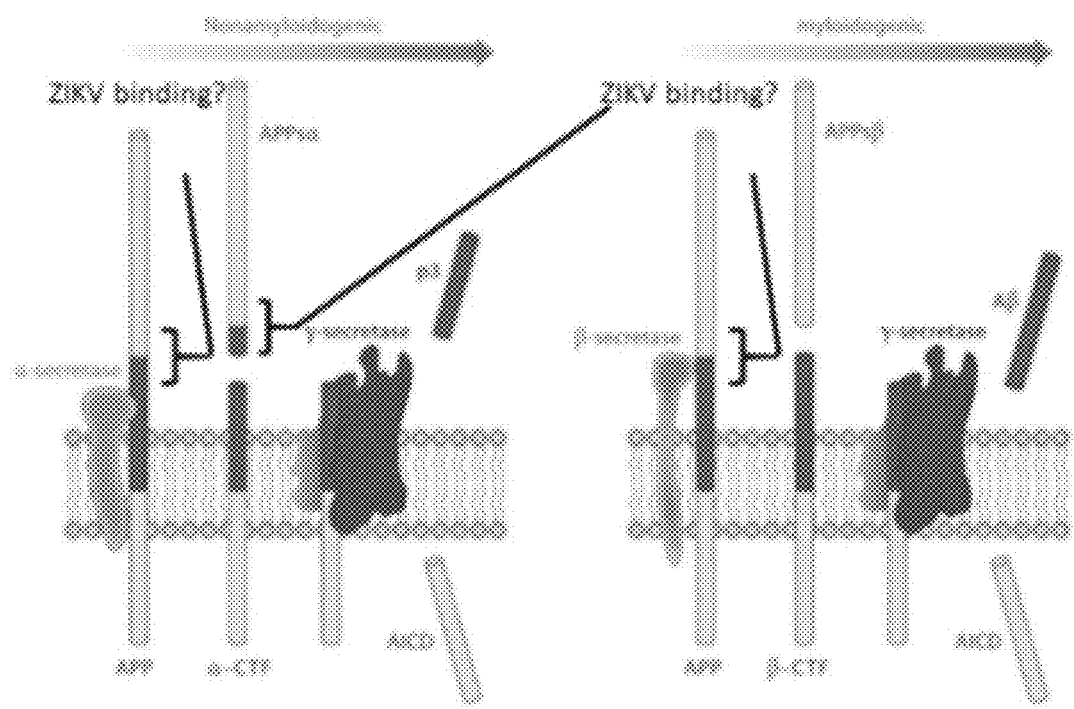
FIGS. 7A-7B: Sequential cleavage of APP occurs by two pathways. APP has large, biologically active, N-terminal ectodomains and a shorter C-terminus. The Aβ peptide starts within the ectodomain and continues into the transmembrane region (red).

Example 2: APP Binds to ZIKV and a Restriction Factor that Serves as a Part of Intrinsic Immunity Against ZIKV in the Brains Amyloid precursor protein (APP) is a membrane protein predominantly expressed in brains and metabolized in a rapid and highly complex fashion by a series of proteases (FIG. 7). The physiological function of APP is not clear. However, APP is involved in Alzheimer's disease development (FIG. 7).

APP is Induced Systematically in STAT2-Null Mice

ZIKV cannot infect immunocompetent mice efficiently, but STAT2-null mice are susceptible to ZIKV. We tested weather APP was modulated by ZIKV in other organs in STAT2-null mice. Mice were infected with ZIKV for various times and euthanized for tissue collections. APP protein levels were increased in splenocytes as early as Day 2 post infections (dpi 2). However, APP expression in the lung were not increased at dpi2 but increased at dpi 4 and 5 (FIG. 8A, top panel). APP were highly expressed in both splenocytes and lung at dpi 8 (data not shown, but the relative levels are included in FIG. 8B). In the brains, no obvious APP expression changes were observed by this assay, maybe related to the high levels of APP in the brains already (data not shown). In addition, APP was also increased in the testis with ZIKV infection (FIG. 8A). However, we did the experiment only once with 4 mice and one-time point (dpi 8). More experiments are needed for a definite conclusion on testis. However, those data suggest that APP protein is induced in a systematic fashion by ZIKV infections.

Generation of an APP and STAT2 Double Knockout Mouse Strain (DKO)

ZIKV NS5 promotes proteasome degradation of human signal transducer and activator of transcription 2 (STAT2). Because STAT2 is a critical mediator of Type I IFN signaling, ZIKV limits the IFN response during human infection. However, ZIKV NS5 does not destroy mouse STAT2, allowing an efficient and effective IFN response. ZIKV cannot infect immunocompetent mice efficiently, but STAT2-null mice are susceptible to ZIKV. Therefore, the role of APP in ZIKV-mediated pathogenesis may be best illustrated in STAT2-null background that represents a similar situation to ZIKV infections in humans.

Figure 9A:
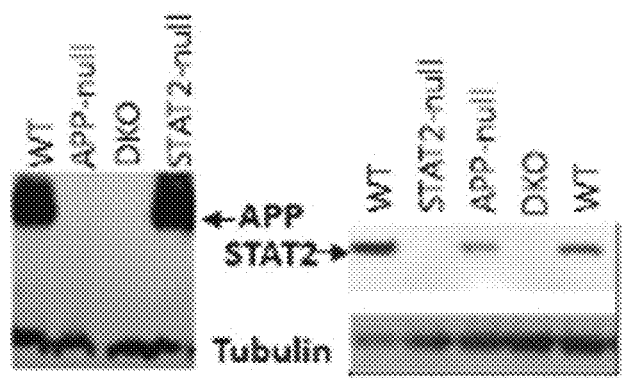
FIGS. 9A-9C. Generation of an APP and STAT2 double knockout mouse strain (DKO).
Figure 9B:
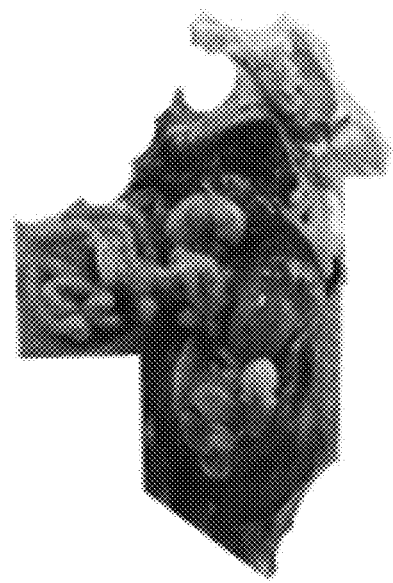
Figure 9C:
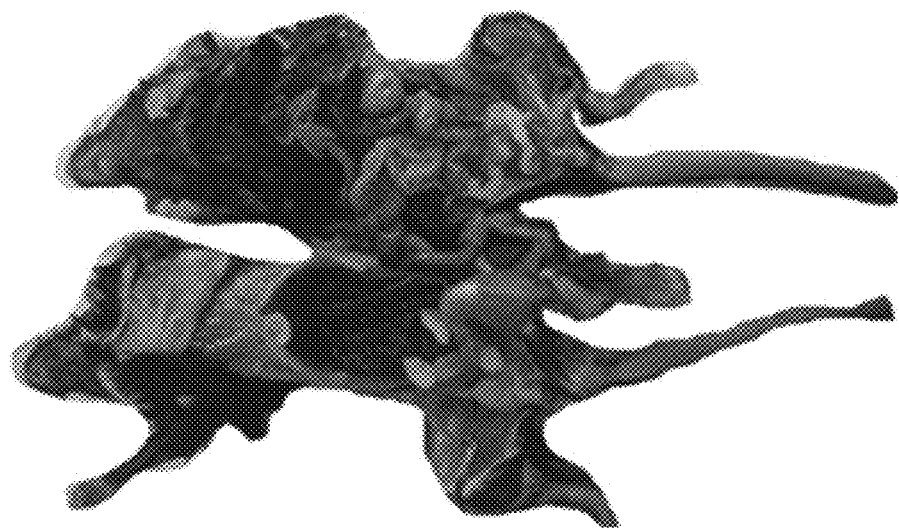

APP-null and STAT2-null mice, both on C57BL/6 background, were crossed for double knockout genotype (DKO; app-/-; stat2-/-). We first confirmed DKO mice with genotyping experiments (data not shown), and further with protein expression data (FIG. 9A). With a few DKO mice available, the susceptibility to ZIKV was tested. One mouse had a swelling liver (FIG. 9B), and another had dark (black) intestine (FIG. 9C). In addition, one mouse had liver changed colors (data not shown). Because only few mice were used, we could not get any conclusions from the initial test. However, with our knowledge, those pathogenic outcomes are apparently not reported in other mouse models for ZIKV.

Example 3: APP Mechanism of Action for Anti-ZIKV Effects

Figure 4:
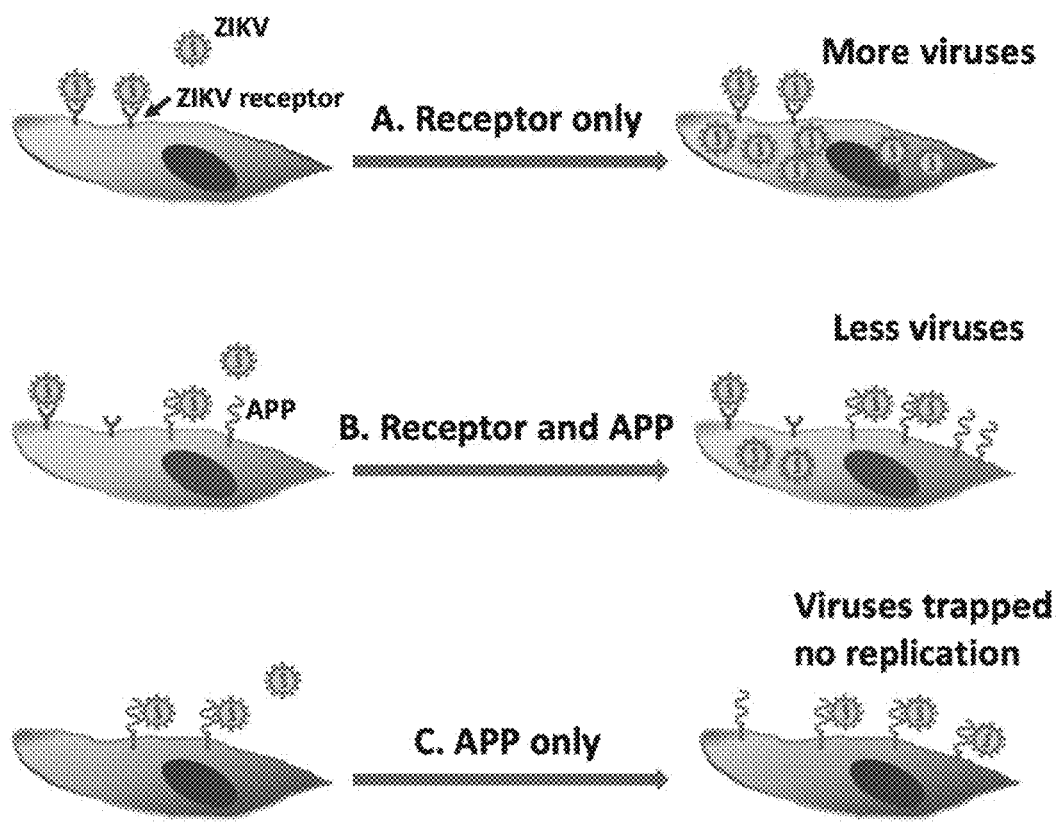
FIG. 4: Model for APP as a restriction factor for ZIKV. APP could inhibit ZIKV replication in both susceptible (indicated with a receptor presence) and insusceptible cells (indicated by the lack of receptor). Situation A: APP would play no role in a susceptible cell without APP expression; Situation B: in a susceptible cell with APP expression, APP would intercept ZIKV during viral infection by serving a decoy receptor. Furthermore, APP protein expression is increased with the interactions, which in turn may bind to more viruses. Only a fraction of the viruses would enter the target cell for replication; Situation C: in an insusceptible cell with APP expression, the attachments to APP would reduce the overall viral burdens and availability in the host, and would lead to the inhibition of the viral replication as a whole.

As demonstrated in Example 1 and Example 2, 1) APP is apparently another binding target of ZIKV (FIG. 1). 2) ZIKV enhances APP expression via multiple mechanisms (FIGS. 2 and 8). 3) APP is apparently a negative regulator for ZIKV replication in both human NPCs/NSCs and neonatal mouse brains (FIG. 3). Based on the facts that APP is predominantly expressed in the brains, APP fits perfectly the definition as a viral restriction factor in the brains. Our data provides a reasonable mechanism for APP as a restriction factor for ZIKV: APP traps ZIKV as a decoy receptor and prevent its replication in the brains. ZIKV also enhance APP expression, which further exacerbates host's antiviral effect. If a susceptible cell with no APP expression, the cell fully supports ZIKV replication (FIG. 4, situation A). As additional APP may trap viruses, ZIKV replication is impaired (FIG. 4, situation B). Another extreme situation is that cells are not susceptible for ZIKV infection by lacking ZIKV receptors or some essential factors. However, if APP are expressed in those cells, APP can still prevent ZIKV virus infection to other infectable cells by trapping the viruses (FIG. 4, situation C). However additional mechanisms are likely present in APP-expressing cells for anti-ZIKV effects. How does ZIKV Increase the Expression of APP In Vivo?

Figure 8:
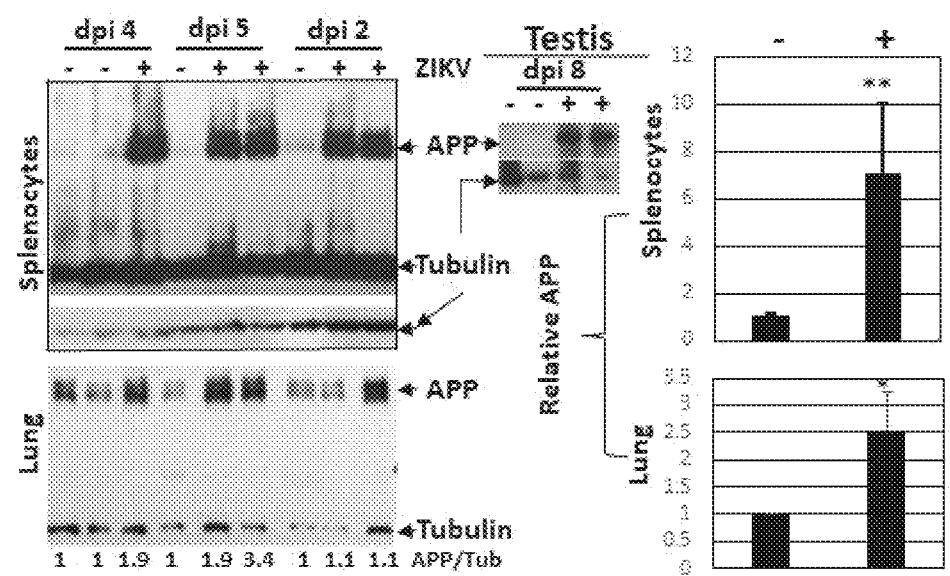
FIG. 8: Systematic induction of APP in spleen and lung after ZIKV infection. STAT2-null mice (B6.129-Stat2tm1Shnd/J, Jackson Laboratory; 4-6 weeks old) were used for subcutaneous (s.c.) injections of ZIKV (PRV-ABC59; 1×10^6 pfu) or 1×PBS. At various times (days after infection). Tissues were harvested after euthanization. Splenocytes were isolated by a standard procedure, and Western blots were used to detect APP proteins. A. Same loading sequences for the panel. + or − indicates whether mice were infected with ZIKV or PBS control respectively. Top section represents results for splenocytes and bottom for the lungs. The samples were collected from nine mice with different treatments as shown on the top. Short exposure time is also shown for the splenocytes. Bottom numbers are relative APP expression levels (APP/tubulin) for the lung tissues, and data are normalized to PBS controls. At the corner of the Panel, expression of APP in testis tissues (day 8) are shown. B. Relative expression levels of APP in spleen (top) and lung (bottom) are shown. For the lung samples, results in Day 2 are not included. For both lung and spleen, the relative APP expression levels in dpi 8 are also included. +: ZIKV infected; −: PBS control. Statistical analysis is done. * p<0.05, ** p<0.01.

Hypothesis: A ZIKV-induced factor(s) is responsible for the systematic induction of APP Rationale and Significance: We have found that ZIKV can stabilize APP protein (FIG. 2). However, ZIKV systemically induces APP expression in spleen, lung and possibly testis in vivo (FIG. 8). Because so many cells are affected, it is unlikely that the cells are all attached by viruses for APP stability. It is highly likely that APP induces a soluble factor(s) that in turn increases the expression of APP at a systemic level. Mechanism for systematic APP induction would establish APP as a factor against ZIKV. Moreover, the knowledge of APP increases would benefit other research areas, such as Alzheimer's diseases.

Identify Responsive Soluble Factor(s) Through Cytokines, Gene Expression and Immune Cell Profiling.

Figure 10:
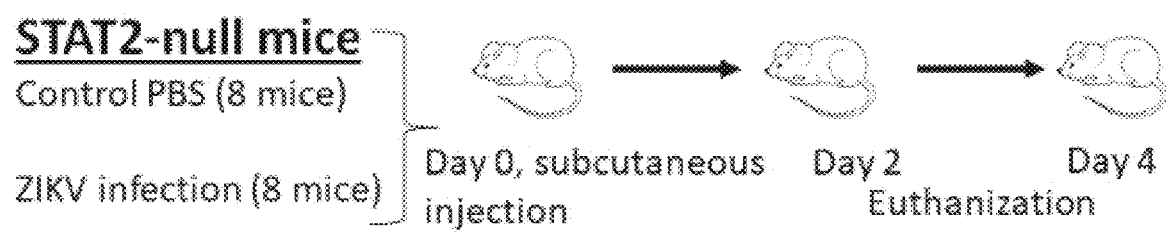
FIG. 10: Mice (6-8 weeks old) are injected subcutaneously with 1) 1×PBS; 2) ZIKV (PRVABC59; 1×10$^6$ pfu). Four mice per group (two males, two females) are examined. Plasma and spleens are collected. Total 16 mice are used.

The induction of APP proteins apparently can last from dpi 2-8 in the spleen. As spleen is one of the major sites for ZIKV replication, we concentrate on splenocytes and choose two early time points (dpi 2 and dpi 4) for analysis the potential changes that are associated with APP expression (FIG. 10).

Cytokine profiles in plasma. Plasma in triplicates are used for cytokine detection using multiplexing technology. We use the Bio-Plex Pro Mouse Cytokine 23-Plex Immunoassay (BioRad), which allows simultaneous assay for 23 mouse cytokines for each sample including IFNγ, IL-1, -6, and TNFα. IL-1β, IL-6, IFNγ, and TNFα are highly expressed upon ZIKV infection at both time points.

Gene expression profiles in splenocytes. Splenocytes are isolated from mice and separated into two parts: one for RNA isolation, another for FACS analyses. RNAs are extracted and subjected for a next-generation RNA sequencing (RNA-seq) analysis. The sixteen samples are multiplexed and distributed on a single NextSeq HighOutput Flowcell V2 75 cycles to generate approximately 16 to 20 million 75 bp single reads per sample. After the initial quality control step to remove low quality reads or nucleotides, all processed RNA-Seq reads are mapped onto the reference human genomes using Bowtie with up to two base mismatches allowed per read. Numbers of reads in genes are counted by the HTSeq counting tool with gene annotations. For pair-wise comparisons, the edgeR package with TMM normalization method is used to analyze the numbers of reads aligned to genes and to identify differentially expressed genes. A threshold value for fold-change of differential expression is set at Fold Change>2, and the adjusted P-values<0.001 are used to reject the null hypothesis. By comparing gene expression profiles, specific and common genes targeted by ZIKV are identified. We perform additional analysis for functional classification, gene ontology term enrichment test, canonical pathway analyses, Ingenuity Pathway Analyses; and database and literature mining. We obtain a whole picture of the RNA targets and signaling pathway. We identify: 1) top four pathways that are the most significantly regulated by ZIKV; 2) cell type changes based on specific lineage marks; 3) major ZIKV targets; and finally 4) APP mRNA levels after ZIKV infection.

Determination which cell population(s) expresses APP. First, we use several commercially available APP antibodies to conjugate with PE and identify proper antibodies and conditions for analyses of APP-expressing cells in splenocytes from ZIKV infected mice. Once the condition is established, we combine with other antibodies with proper labels for analyses of variety of specific cells. Our FACS Core Facility have capacity to analyses 16 different lasers simultaneously. The proportion of cells, and the levels of APP expression are obtained. Many kinds of cells play a role in anti-ZIKV responses. We initially check the proportion of the CD4 and CD8 T lymphocytes, Treg (CD25), B lymphocytes, NK cells, macrophages, dendritic cells with their specific markers. We combine all the data together and analyze. All information would lead to clues for a putative factor(s) that might lead to high APP expression.

Determine Whether Identified Putative Factor(s) can Induce APP Expression In Vivo Once we have the putative targets for induction of APP in vivo, we first use the factor(s) to treat STAT2-null mice. Basically, nine mice are used (3 for PBS, 6 for cytokine combinations with various concentrations). Putative cytokine(s) in combinations are used to treat the target mice and two days later, the mice are euthanized and splenocytes are examined by FACS and Western Blot for APP expressions. The cytokines are chosen based on the signaling pathways activated by ZIKV infection and cells for APP expression. Second, if blocking agents or antagonists are available, such as IL6 antibody, we test whether blocking the cytokine would affect ZIKV-mediated APP expression. ZIKV is used to infect STAT2-null mice and at the same time, single or multiple antagonists are injected. Whether those antagonists could alter the induction of APP is examined two days later as in FIG. 8. If a cytokine were involved, APP levels should have statistically significant changes in response to the cytokine manipulations.

Outcomes: A cytokine(s) and a cell type(s) is identified to be associated with APP induction in vivo. It is possible that several cytokines together may induce APP expressions in vivo. Currently, IL-6 and IL-1B are the two major candidates for APP mRNA inductions. However, if APP mRNA is not changed accordingly, IL-1B is the primary candidate as it enhances APP mRNA translation efficiency. These experiments may establish that APP may not just a restriction factor for the host brain, but also an inducible factor against ZIKV in innate immunity.

Alternative Strategies: A. Plasma ApoE levels are measured after ZIKV infection because ApoE induces APP mRNA expression in human neurons. If ApoE is increased upon ZIKV infections, we test if ApoE treatment could increase APP in splenocytes in vitro and in vivo. B. If in vivo induction by cytokines are not working properly, we inject cytokines plus inactivated ZIKV. Maybe the cytokines plus ZIKV virions might have some unexpected outcomes. C. In vitro induction assay is used. Basically, the target primary cells are sorted out with flow cytometry from an uninfected mouse. The cytokine(s), with or without ZIKV, are used for ZIKV infection and the cells are examined by FACS or Western Blot for APP expressions two days later. D. The test for in vivo induction with antagonist might be a challenge. A combination of multiple antagonists might be necessity. If Alternative C is working, we test the antagonists in combination in an in vitro setting first, before moving to in vivo experiments. E. No sex differences are expected.

How does a Viral Peptide Enhance APP Expression?

Hypothesis: ZIKV peptide binds to APP directly to disrupt APP proteolytic processing.

Rationale and Significance: A peptide is identified to stabilize APP expression (FIG. 2I). Because of the structural similarity to BACE1 (FIG. 1A-1C) and binding to APP may affect its stability and processing, the peptide may adhere to APP via BACE1 cleavage site, change the conformation of APP, and slow the whole proteolytic process. The research on the peptide would reveal the mechanism for ZIKV to stabilize APP. Moreover, knowledge here may provide a target for antiviral treatment and benefit other research areas.

Determine Whether the Viral Peptide Interact with APP Directly

The peptide (P2) could enhance the expression of APP, apparently through the stabilization of APP protein (FIG. 1). We evaluate if the physical interactions play a role in the stabilization of APP protein.

First, we generate a P2-based peptide antibody. A P2SA peptide, GMI VND TGH ETD ENR AKV EI (SEQ ID NO:19), 20-aa stretch from the P2 sequence, is synthesized with an addition of cysteine in the N-terminus and sent out for antibody production. The peptide sequences were analyzed and found to be good for generating antibodies based on available programs. We test if rabbit sera are reacting with P2 properly. If the peptide antibody was not working properly, we synthesize two new P2 peptides with FLAG tag linked to N- and C-terminus respectively. Whether the FLAG-P2s enhance APP expression is examined. If they work, we use the FLAG-P2 for experiments below with FLAG antibody instead. Second, we transfect P2 peptide with APP-expression plasmid into HEK293 cells and examine their potential interactions. We do: 1) Co-immunoprecipitation (Co-IP) experiments. APP and P2 peptide antibodies are used for co-IP experiment as shown in FIG. 1J. 2) Chemical cross-linking assays: the non-cleavable NHS-ester cross-linker is used to "fix" potential P2 and APP interactions, and the "fixed" complex is immunoprecipitated with either APP or P2 antibody. 3) Whether P2 peptide are co-localized with APP is tested by co-immunoprecipitation experiments as shown in FIG. 1K. And 4) Using radioactive labeled P2 peptide. P2 peptide is labeled with carbon 13 (C13)-leucine (L). The leucine is chosen because the P2 peptide contains four leucine residues (FIG. 1C). Whether APP can bring down C13-labelled P2 peptide is tested. All results address the question of the interactions. With interaction between ZIKV and APP established (FIG. 1), the P2 peptide should interact with APP.

We test whether the P2 peptide could interact with one of the processed APP product. The sAPPα has majority of APP's ectodomain and contains the predicted ZIKV-binding site (FIG. 7). sAPPα proteins are commercially available, and might be the best reagent for testing the direct interaction with P2 peptide. Similar approach as above are employed by mixing sAPPs and P2 peptides under different conditions. If sAPPα were able to interact with P2 directly, we test if sAPPα is able to interact with ZIKV and inhibit ZIKV replication in NPCs/NSCs. The results may show that sAPPα is a soluble "decoy receptor" for ZIKV.

Determine if Alternation of APP-Peptide Interactions Affects Peptide-Mediated APP Stabilization Whether P2 peptide affects APP processing in transfected cells is examined. Basically, we transfect APP expression plasmid into cells, with or without P2 peptide. The expression of APP processed products, amyloid beta 42 (Aβ42), Aβ40, soluble Aβ precursor protein alpha (sAPPα), sAPPβ and APP intracellular domain (AICD), is examined in both media and cell lysates. The routine ELISA and Western blot analyses are employed depending on the targets. Reagents are selected carefully as some precautionary notes present. The difference in APP processing with or without P2 peptide, both in quality as well as quantities are obtained. The critical cleavage site(s), influenced by ZIKV binding, is/are determined based on cleavage products. In addition, some new peptide(s) or cleavage site(s) may be generated. The new peptides are further examined by The Proteomics Core Facility at UNL.

Whether P2-APP interaction affects APP processing and stability is tested. We: A) compare the behavior of P2 and P2SA peptide. P2SA peptide (used for antibody production) does not interact with APP. We compare the two peptides in their ability to interact with APP and their capacity to increase APP expression. B) make a deletional mutagenesis in APP expression plasmids and remove the potential interacting site with ZIKV and P2. Whether the mutant APP protein has a defect in its processing, interaction with and enhancement by P2 peptide is examined in HEK293 cells. The result implicates the role of P2-APP interaction in APP processing and enhancement.

Other than protease processing, whether proteasome pathway plays a role in ZIKV-mediated APP stabilization in vitro is be determined. APP and its processed product accumulations are affected by ubiquitination. It is possible that ZIKV affects proteasome pathway and in turn stabilizes APP proteins. We make a mutagenesis in APP expression plasmids and change three lysine residues into arginines (aa #724-726; from NM_201414.2). It has been reported that the mutant (APP3R) has drastically reduced the ubiquitination levels of APP at least in Hela cells. Whether the APP3R mutant protein is enhanced by the ZIKV infection is tested in HeLa as well as HEK293 cells. The result implicates the role of ubiquitination in ZIKV-mediated enhancement of APP protein. Second, the proteasome inhibitors, lactacystin and M132, are used to treat cells followed by ZIKV infection, and APP expression is then examined. Whether reduction of ubiquitin (via siRNA targets Ub) and Ub overexpression has an effect on ZIKV-mediated APP stabilization is also determined. Because the ubiquitination process affects APP processing, ZIKV may influence the proteasome pathway, and through which, eventually affect proteolytic processing of APP. Whether P2 increases APP RNA is also examined. APP mRNA's alternation during ZIKV infection is also tested. However, given the nature of the P2 peptide, it is unlikely that P2 could enhance the mRNA levels of APP.

Determine if ZIKV Uses Similar Mechanism for Enhancement of APP Expression

The P2 peptide offers a simple and effective system for APP stability studies. We assess the mechanism of ZIKV-mediated enhancement (FIG. 2). ZIKV may use a similar mechanism as P2 peptide and similar techniques are employed. In addition, ZIKV may use more mechanisms than P2 peptide for APP regulation. The mechanism for ZIKV-mediated APP enhancement in vitro is revealed.

Outcomes: 1) An ZIKV P2 peptide may be interacting with APP; 2) APP processing may be affected by P2 peptide; or 3) APP processing and P2 interactions are correlated. With several alternative approaches, the mechanisms of P2 peptide and ZIKV to enhance APP expression are inferred. We predict that both P2 peptide and ZIKV interact with APP, alter and slow down the APP proteolytic process, and eventually increase APP expression. Other mechanisms may also be present and are examined in a systemic manner. The potential usage of the P2 peptide as a therapeutic agent is inferred.

Alternatives: If results related to P2 peptide are not satisfying, we use a ZIKV virion to address the same issue. In addition, we address whether alternation of endogenous protease target affects the ZIKV mediated APP stabilization. What is the General Role of APP in ZIKV-Mediated Pathogenesis?

Hypothesis: APP inhibits ZIKV replication in a systematic manner.

Rationale and Significance: APP is inducible in several organs after ZIKV infection (FIG. 8). As APP is a restriction factor for ZIKV (FIG. 3), APP may modulate ZIKV replication and related pathogenesis in a systemic manner. ZIKV NS5 targets human and mouse STAT2 differently, and ZIKV infects STAT2-null mice efficiently. We generated a double knockout mouse strain (DKO, stat2−/−, app−/−). Therefore, the role of APP in ZIKV infection can be assayed in systematic fashion. A complete picture about the role of APP as an anti-ZIKV gene and related pathogenesis is documented.

Determine the Roles of APP in Systemic ZIKV Infection by Comparing STAT2-Null and DKO Mice APP has restricted expression in other organs/tissues. In addition, we used a very few DKO mice and found some interesting pathogenic outcomes (FIG. 9B-C). Because ZIKV increases APP expression outside the brain (FIG. 8), it is necessary to examine APP's role outside the brain.

Figure 11:
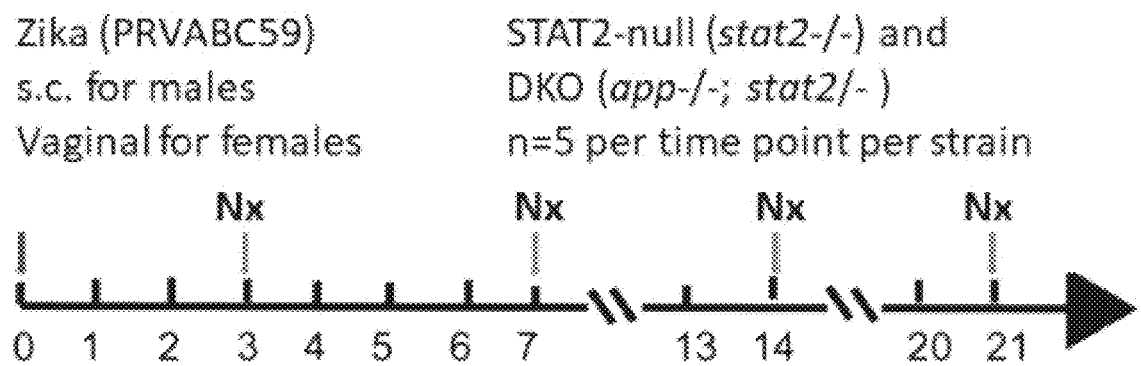
FIG. 11: Mice (6-8 weeks old) are infected by s.c., and vaginal with ZIKV (PRVABC59). The dosages are determined as described in the text. Five mice per time point per strain per treatment are examined. We suspect APP might inhibit ZIKV replication by two fold, with 50% of variation. Five mice per strain are needed to attain statistical significance results with p<0.05 and 90% probability per time point. Total 160 mice (80 females, 80 males) are needed for the experiments.

First, we titrate ZIKV PRVABC59 on the new DKO (app−/−; stat2−/−) strain. Basically, three DKO mice (three females) are infected with ZIKV (vaginal injection) with three dosages ($10^4$, $10^5$, $10^6$ pfu) are used for vaginal injection. Mouse weights (every day) and virus titers in the blood (every two days) are monitored through 8 days. The dosage(s) that cause weight loss, viremia, but not killing the mice in first 8 days are chosen for further experiments. Second, adult male mice are inoculated with ZIKV (PRV-ABC59, $10^4$ pfu) through s.c. injections and female mice are inoculated with ZIKV (dosage determined by titrations) via vaginal inoculation as described (FIG. 11). Those mice are euthanized on dpi 3, 7, 14 and 21 (FIG. 11). Plasma is collected every other day before euthanasia. Tissues (testis, ovary, kidney, small intestine, lung, brain, spleen, liver, vaginal tracks, and plasma) after euthanasia are collected. One portion is fixed in 4% paraformaldehyde (PFA) and a small portion of testis tissue is also fixed in modified Davidson's fluid for morphological analysis. The other portion of tissues is frozen immediately. Viral loads are detected using qRT-PCR and plaque assay. If mice survive 21 days, results from 14 and 21 dpi would show whether APP play a role in anatomical sanctuary sites for persistent infection after viremic resolution. The role of APP in ZIKV pathogenesis emerges.

Outcomes: A) The role of APP in ZIKV infection and pathogenesis is systematically revealed, and possibly as an inhibitor. Novel pathogenic phenotypes may be identified as in FIG. 9. B) if observed pathogenic changes are repeated (FIG. 9b, 9c), we do a RNAseq analyses for the target organ/tissue and identify the associated gene expression and pathway changes. The role of APP in the putative pathogenesis is inferred. In addition, cells infected by ZIKV are also identified.

Alternatives: A) The standard 6-8-week old mice are chosen for the experiments. If the results, especially the pathogenesis, are moderate, we choose older mice (4-6-month olds), because the DKO mice for initial test were all aged ones (>4-month-old, retired mice) (FIG. 9). B) Because African ZIKV strains induce short episodes of severe neurological symptoms followed by lethality, African ZIKV strain (MR766) are also used as the strain used is considered a weak one.

Does APP Inhibit the Formation of Microcephaly During ZIKV Vertical Transmission?

Hypothesis: APP inhibits ZIKV replication in fetal brains, thereby decreasing the risk of microcephaly.

Rationale: APP is expressed in embryos. Fetal brains are readily infected by ZIKV. APP has a stronger anti-ZIKV effect in newborn mouse brains (P4 and P7) (FIG. 3E), which may be related to the fact that neonatal mice have a higher proportion of NPCs/NSCs in the brains. Because fetal brains have plenty of NPCs/NSCs, APP may exert similar anti-ZIKV effects as in neonatal mice. Therefore, APP would protect NPCs/NSCs from ZIKV-mediated killings, thereby rendering a protective role in microcephaly.

Significance: The role of APP in ZIKV-mediated fetal brain disruption is established, and a model for ZIKV-mediated brain damages, possible for microcephaly, is generated.

Determine if APP Reduces ZIKV-Mediated Fetal Brain Injury During Vertical Transmission Fetal brains express APP and decent portion of NPCs/NSCs. It is possible that APP is also anti-ZIKV gene in fetuses and prevent the development of microcephaly.

Figure 12A:
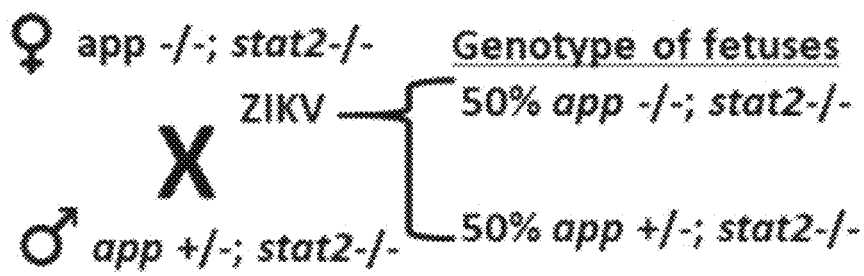
FIGS. 12A-12B.
Figure 12B:
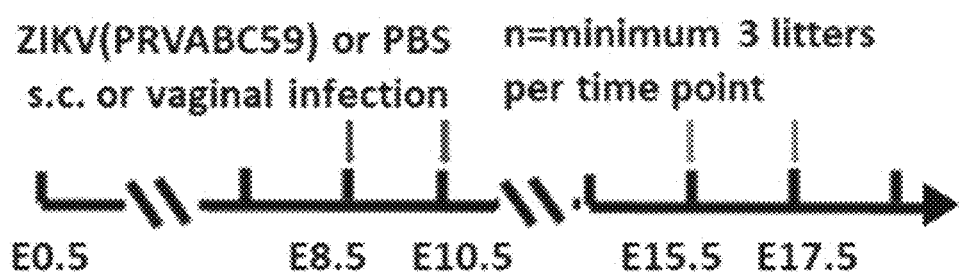
Figure 13A:
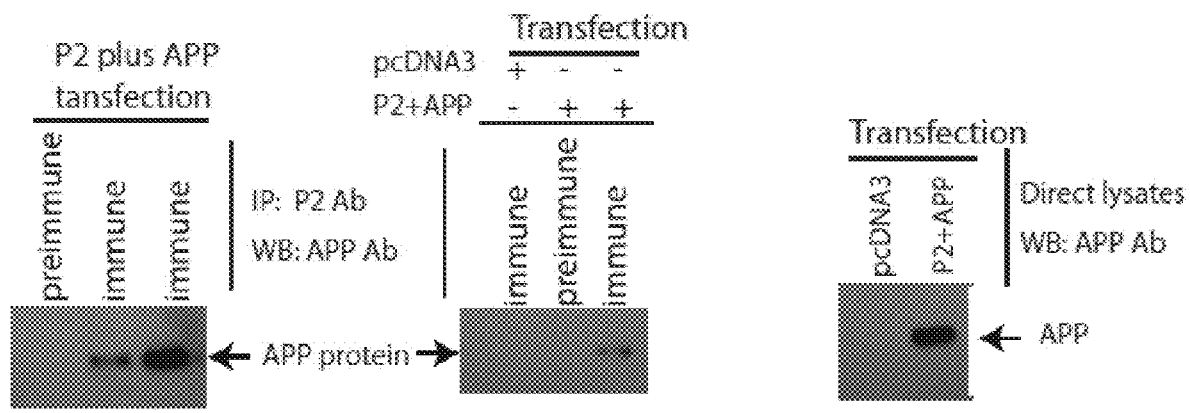
FIGS. 13A-13B: P2 polypeptide reduces amyloid formation as demonstrated by Western blot (FIG. 13A) and immunofluorescence (FIG. 13B).
Figure 13B:
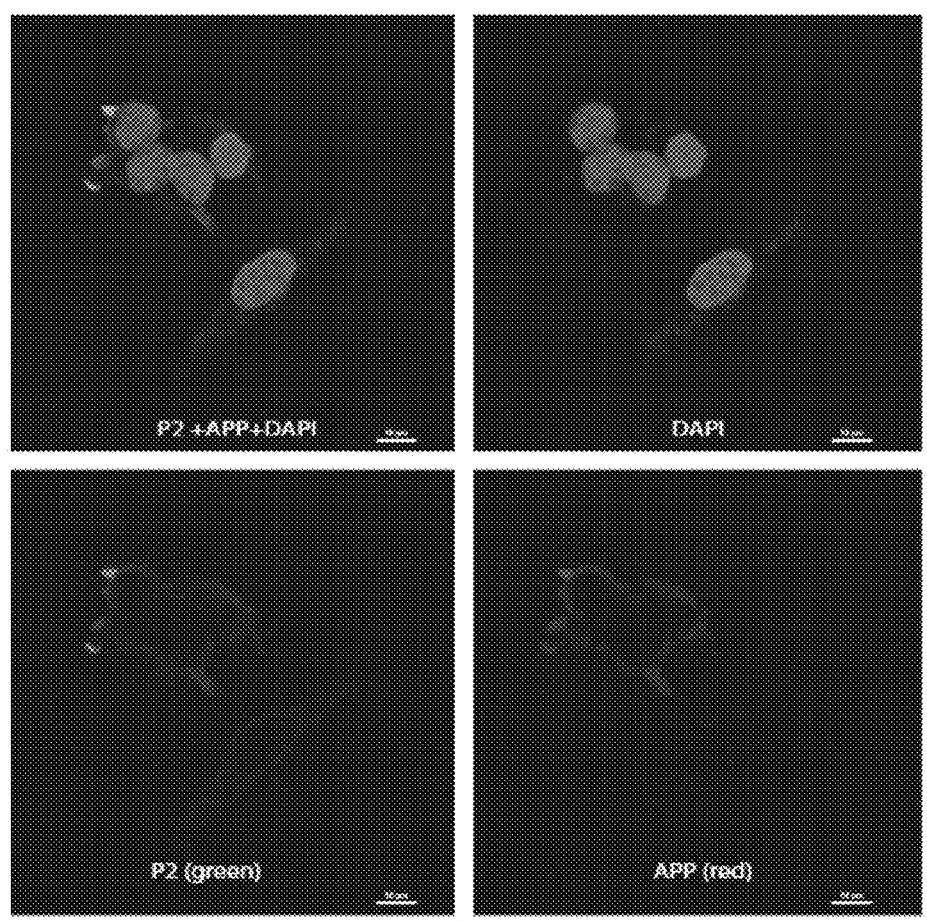

To study the fetal brain changes during ZIKV infection of pregnant mice, we use the DKO (app−/−, stat2−/−) dams and heterozygous (app+/−, stat2−/−) sires that are obtained by crossing the DKO and stat2-null mice (FIG. 12a). Each mating group consists of 1 male and 3 female mice that are 6-15-week old. At the start of the dark cycle, the mating group is put into a new cage for overnight mating. Early next morning, female mice are checked for the presence of a vaginal plug. Pregnancy is timed by the presence of a plug as embryonic days 0.5 (E0.5). We have two groups of mice in this study. The first is the fetal-ZIKV group comprised of three pregnant dams that are infected with ZIKV. The second is the fetal-control group comprised of three pregnant dams that are inoculated with PBS. We use s.c. injection as it represents majority of human infection during pregnancy, unless vaginal infection is better. Pregnant dams are infected at E8.5 or E10.5. The fetuses are collected on the E15.5 and E17.5 (FIG. 12b). The reasons for picking up those dates are: 1) Earlier than E7.5 infection might cause severe mouse demise. Infection on E8.5 may not generate an obvious body defect on E17.5 in IFN-null fetuses. Because we expect an increase in viral loads in APP-null background, the E8.5 and E10.5 are our target dates for viral injection, and E15.5 and E17.5 are targets for collections. In addition, lower dosage are used. The reasons to pick three dams for each time point for initial examination are: 1) STAT2-null dams may have 6-8 fetuses per litter. And with ZIKV infection, the number dropped to 4-6, we assume six (three DKO, and three APP-positive) fetuses per litter for pregnant DKO dams in FIG. 12A). 2) As only one allele of app (+/−) in fetuses, the function of APP might be reduced in those mice. APP might inhibit ZIKV replication by two-fold, with 50% of variation. It is calculated that 9 fetuses (or three dams) are needed to attain data with statistical significance p<0.01 with 95% probability.

We: 1) measure the fetus body and head sizes. The fetal body sizes are measured by crown-rump length (CRL) and head sizes are obtained by occipito-frontal (OF) diameter; 2) determine the gene types of fetuses. Not only the fetuses, but also resorbed fetuses and conceptuses if present, are subject to genotyping; 3) examine fetal brain structural changes. Fetal brains are fixed by PFA. The gross morphology of the affected brains is visualized with the Nissl Stain. The thickness of marginal zone (MZ), cortical plate (CP), subplate (SP), intermediate zone (IZ), subventricular zone (SVZ), and ventricular zone (VZ) are measured; 4) determine viral load in the brains. A portion of the fetal brains is used for viral loads detections; 5) determine the percentage of cells infected by ZIKV, apoptosis and proliferation. The brain sections are stained with ZIKV, activated Caspase 3, phospho-Histone H3 antibodies, and DAPI simultaneously. The number of the positive cells is counted and quantified; 6) determine the nature of brain cells: NeuN (a marker for neurons), TBR1 (early and immature neurons marker), Nestin and Sox2 (Neural progenitor/stem cells marker) are used for staining. The positive cells are counted and thickness of the layers stained with markers are quantified; 7) determine the identity of ZIKV-infected cells. Antibodies for ZIKV and specific markers (determined in 6) are used to determine the identity of ZIKV-infected cells. Due to emission overlaps, maximum 3 antibodies plus DAPI can be used for Confocal imaging studies. State-of-the-art imaging technology is used in UNL Microcopy Core Facility.

Outcomes: 1) The advantage of the design (FIG. 12A) is that the two genotypes of fetuses can be located in one litter, which would make the comparison of the target phenotypes more reliable and accurate. Fetus body and head sizes, viral yields, gross morphology, percentage of ZIKV infected cells, apoptotic, and proliferating cells, the nature of neurons affected by ZIKV in various time points are obtained in quantitative manner. Based on the genotypes, those parameters are compared and analyzed in a statistical manner. Once statistical significant ($p<0.05$) parameters are identified, whether those parameters are related to certain brain damages and possible linkages to microcephaly are investigated. If APP behaves as we hypothesized, some if not all of the phenotypes may be observed in DKO fetuses: a smaller head size, thinning of the cortical zones, reduction of Sox2/nestin positive cells, increase of apoptotic cells, decrease in proliferating cells, higher viral load, and ZIKV mainly infect NPCs located in the ventricular and subventricular zones of the fetal mouse cortex. 2) A condition may be identified to generate certain percentage of baby mice with microcephaly. 3) Some unexpected results are also possible, just like the role of IFNs in fetal development. Decent amounts of information are obtained for analyses.

Alternatives: A) Timing for infection and dissection of fetuses may need to be adjusted because the proposed schedules are based on literatures and our data. B) Number of dams may need be increased if statistical power is not reached. C) Use of IFN-receptor antibodies as alternative. Basically, incrossed and pregnant dams (WT and APP-null) are treated with IFNAR antibody every two days, starting on the Day-1, relative to ZIKV infection. IFNAR-blocking mAb and its control are available commercially. Fetuses and placentas are harvested for studies. The analyses are the same as described above. Because pregnant mice with the antibody still made enough IFNs to partially control the infection, the best approach would be the use of DKO mice. D) IFNs cause intrauterine growth restriction (IUGR). As the role of APP is examined in an STAT2-null background, IUGR might not be a problem.

Together these experiments shed light on a novel intrinsic immunity against ZIKV. With the completion of the proposed experiments, we may establish the role of APP in ZIKV infection and pathogenesis and a model for microcephaly in rodents, which would represent a vertical advance in both ZIKV and microcephaly research. Nevertheless, the research may provide important information on how to prevent and treat ZIKV-related diseases. Moreover, the research may benefit brain diseases studies in general.

Example 4: P2 Polypeptide Reduces Amyloid Formation

P2 interacts with APP and block APP metabolic processing, and reduce amyloid formation (FIG. 13).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing Aβ-amyloid plaque formation in a mammal having Alzheimer's disease (AD), wherein said method comprises administering to said mammal a polypeptide comprising, the amino acid sequence set forth in SEQ ID NO:1.

2. The method of claim 1, wherein said mammal is a human.

3. The method of claim 1, wherein said polypeptide is administered intraperitoneally, intravenously, intramuscularly, or subcutaneously.

* * * * *